(12) United States Patent
Portoghese et al.

(10) Patent No.: US 10,464,941 B2
(45) Date of Patent: Nov. 5, 2019

(54) THERAPEUTIC COMPOUNDS

(71) Applicant: REGENTS OF THE UNIVERSITY OF MINNESOTA, Minneapolis, MN (US)

(72) Inventors: Philip S. Portoghese, Minneapolis, MN (US); Eyup Akgun, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/553,524

(22) PCT Filed: Feb. 24, 2016

(86) PCT No.: PCT/US2016/019374
§ 371 (c)(1),
(2) Date: Aug. 24, 2017

(87) PCT Pub. No.: WO2016/138142
PCT Pub. Date: Sep. 1, 2016

(65) Prior Publication Data
US 2018/0237447 A1    Aug. 23, 2018

Related U.S. Application Data

(60) Provisional application No. 62/120,226, filed on Feb. 24, 2015.

(51) Int. Cl.
| | |
|---|---|
| *C07D 498/08* | (2006.01) |
| *A61K 31/485* | (2006.01) |
| *C07D 489/08* | (2006.01) |
| *A61K 45/06* | (2006.01) |
| *A61K 47/54* | (2017.01) |
| *A61P 29/00* | (2006.01) |
| *A61K 31/4545* | (2006.01) |
| *A61K 47/55* | (2017.01) |

(52) U.S. Cl.
CPC ........ *C07D 489/08* (2013.01); *A61K 31/4545* (2013.01); *A61K 31/485* (2013.01); *A61K 45/06* (2013.01); *A61K 47/54* (2017.08); *A61K 47/55* (2017.08); *A61P 29/00* (2018.01)

(58) Field of Classification Search
CPC ............................ C07D 498/08; A61K 31/485
See application file for complete search history.

(56) References Cited

U.S. PATENT DOCUMENTS

2009/0233841 A1    9/2009 Portoghese et al.

FOREIGN PATENT DOCUMENTS

| WO | 2012109464 A2 | 8/2012 |
| WO | 2014124317 A1 | 8/2014 |

OTHER PUBLICATIONS

"Organic chemistry portal", https://www.organic-chemistry.org/snyhesis/C1N/carbamates.shtm, accessed Dec. 9, 2018, attahched as pdf (Year: 2018).*
"Organic chemistry portal", https://www.organic-chemistry.org/synthesis/C1N/amines/amines.shtm,accessed Dec. 9, 2018, attached as pdf (Year: 2018).*
"Organic chemistry portal", https://www.organic-chemistry.org/synthesis/C1O/esters1.shtm,accessed Dec. 9, 2018, attached as pdf (Year: 2018).*
"Organic chemistry portal", https://www.organic-chemistry.org/synthesis/C1O/arylethers1.shtm,accessed Dec. 9, 2018, attached as pdf (Year: 2018).*
Yuan. Organic and Biomolecular Chemistry, 2012, 10, 2633 (Year: 2012).*
Aceto, et al., "MDAN-21: A Bivalent Opioid Ligand Containing mu-Agonist and Delta-Antagonist Pharmacophores and Its Effects in Rhesus Monkeys", International Journal of Medicinal Chemistry 1-6 (2012).
Akgun, et al., "Induction of heterodimerization of mu opioid peptide (MOP) and type-2 cholecystokinin (CCK2) receptor by novel bivalent ligands", Drugs Fut 33 (Suppl. A): XXth Int Symp Med Chem (Aug. 31-Sep. 4, Vienna) (2008).
Akgun, et al., "Inhibition of Inflammatory and Neuropathic Pain by Targeting a Mu Opioid Receptor/Chemokine Receptor5 Heteromer (MOR-CCR5)", J. Med. Chem. 58 (21), 8647-8657 (2015).
Akgun, et al., "Ligands that interact with putative MOR-mGluR5 heteromer in mice with inflammatory pain produce potent antinociception", PNAS vol. 110 (28), 11595-11599 (2013).
Bhushan, et al., "A Bivalent Ligand (KDN-21) Reveals Spinal δ and κ Opioid Receptors Are Organized as Heterodimers That Give Rise to δ1 and κ2 Phenotypes. Selective Targeting of δ-κ Heterodimers", J Med Chem 47, 2969-2972 (2004).
Chen, et al., "Heterodimerization and cross-desensitization between the mu-opioid receptor and the chemokine CCR5 receptor", Eur J Pharmacol 483, 175-186 (2004).
Cherny, et al., "Opioid responsiveness of cancer pain syndromes caused by neuropathic or nociceptive mechanisms: a combined analysis of controlled, single-dose studies", Neurology 44, 857-861 (1994).
Daniels, et al., "A Bivalent Ligand (KDAN-18) Containing δ-Antagonist and κ-Agonist Pharmacophores Bridges δ2 and κ1 Opioid Receptor Phenotypes", J Med Chem 48, 1713-1716 (2005).
Daniels, et al., "Opioid-induced tolerance and dependence in mice is modulated by the distance between pharmacophores in a bivalent ligand series", Proc Natl Acad Sci 102(52), 19208-19213 (2005).
Guasti, et al., "Minocycline treatment inhibits microglial activation and alters spinal levels of endocannabinoids in a rat model of neuropathic pain", Mol Pain 5, 35, 10 pages (2009).
Heinrich, et al., "Interleukin-6-type cytokine signalling through the gp130/Jak/STAT pathway", Biochem J 334, 297-314 (1998).
Imamura, et al., "Discovery of a Piperidine-4-carboxamide CCR5 Antagonist (TAK-220) with Highly Potent Anti-HIV-1 Activity", J Med Chem 49(9), 2784-2793 (2006).

(Continued)

*Primary Examiner* — Noble E Jarrell
(74) *Attorney, Agent, or Firm* — Viksnins Harris Padys Malen LLP

(57) ABSTRACT and salts thereof are disclosed. Also disclosed are pharmaceutical compositions comprising a compound of formula I, processes for preparing compounds of formula I, intermediates useful for preparing compounds of formula I and therapeutic methods using a compound of formula I.

18 Claims, 19 Drawing Sheets

(56) References Cited

OTHER PUBLICATIONS

Jorgensen, et al., "Comparison of simple potential functions for simulating liquid water", J Chem Phys 79, 926-935 (1983).
Khasabova, et al., "Cannabinoid Type-1 Receptor Reduces Pain and Neurotoxicity Produced by Chemotherapy", J Neurosci 32(20), 7091-7101 (2012).
Kondru, et al., "Molecular interactions of CCR5 with major classes of small-molecule anti-HIV CCR5 antagonists", Mol Pharmacol 73, 789-800 (2008).
Le Naour, et al., "Bivalent Ligands That Target µ Opioid (MOP) and Cannabinoid1 (CB1) Receptors Are Potent Analgesics Devoid of Tolerance", J Med Chem 56(13), 5505-5513 (2013).
Manglik, et al., "Crystal structure of the µ-opioid receptor bound to a morphinan antagonist", Nature 485, 321-326 (2012).
Nishikawa, et al., "Analysis of Binding Sites for the New Small-Molecule CCR5 Antagonist TAK-220 on Human CCR5", Antimicrob Agents Chemother 49, 4708-4715 (2005).
Padi, et al., "Attenuation of rodent neuropathic pain by an orally active peptide, RAP-103, which potently blocks CCR2- and CCR5-mediated monocyte chemotaxis and inflammation", Pain 153, 95-106 (2012).
Singh, et al., "Minocycline attenuates HIV-1 infection and suppresses chronic immune activation in humanized NOD/LtsZ-scidIL-2Rynull mice", Immunology 142, 562-572 (2014).
Smith, "Treatment Considerations in Painful HIV-Related Neuropathy", Pain Physician 14, E505-524 (2011).
Szeto, et al., "Minocycline Attenuates HIV Infection and Reactivation by Suppressing Cellular Activation in Human CD4+ T Cells", J Infect Dis 201, 1132-1140 (2010).
Takashima, et al., "Highly Potent Inhibition of Human Immunodeficiency Virus Type 1 Replication by TAK-220, an Orally Bioavailable Small-Molecule CCR5 Antagonist", Antimicrob Agents Chemother 49, 3474-3482 (2005).
Tan, et al., "Structure of the CCR5 chemokine receptor—HIV entry inhibitor Maraviroc complex", Science 341, 1387-1390 (2012).
Uhelski, et al., "Inhibition of anandamide hydrolysis attenuates nociceptor sensitization in a murine model of chemotherapy-induced peripheral neuropathy", J Neurophysiol 113, 1501-1510 (2015).
Weiss, "Derivatives of Morphine. I. 14-Hydroxydihydromorphinone", J Am Chem Soc 77(22), 5891-5892 (1955).
Wilson, et al., "A continuous fluorescence displacement assay for BioA: an enzyme involved in biotin biosynthesis", Anal Biochem 416, 27-38 (2011).
Xie, et al., "Interaction of Bivalent Ligand KDN21 with Heterodimeric δ-κ Opioid Receptors in Human Embryonic Kidney 293 Cells", Mol Pharmacol 68(4), 1079-1086 (2005).
Zhang, et al., "A bivalent ligand (KMN-21) antagonist for µ/κ heterodimeric opioid receptors", Biorg Med Chem Lett 19, 6978-6980 (2009).
Zhang, et al., "Homology modeling and molecular dynamics simulations of the mu opioid receptor in a membrane-aqueous system", ChemBioChem 6, 853-859 (2005).
Zheng, et al., "Induced association of mu opioid (MOP) and type 2 cholecystokinin (CCK2) receptors by novel bivalent ligands", J Am Chem 52, 247-258 (2009).
Cataldo, et al., "Bivalent ligand MCC22 potently attenuates nociception in a murine model of sickle cell disease", Pain 159, 1382-1391 (2018).

* cited by examiner

Figure 13

| Spacer Atom Number | Length (Å) | Control ED$_{50}$/LPS ED$_{50}$ (i.t.) | Control ED$_{50}$/LPS ED$_{50}$ (i.c.v.) |
|---|---|---|---|
| 4 (Monovalent) | | 5.17 | 0.53 |
| 5 (Monovalent) | | 1 | 1 |
| 14 | 16.1 | 3.05 | 1.89 |
| 17 | 19.9 | 33.94 | 1.91 |
| 19 | 22.5 | 14.58 | - |
| 21 | 23.5 | 1.88 | 1 |
| 22 | 26.4 | 3,070 | 1 |
| 24 | 27.5 | 2.75 | - | ns
THERAPEUTIC COMPOUNDS

PRIORITY OF INVENTION

This application claims priority from U.S. Provisional Patent Application No. 62/120,226 filed Feb. 24, 2015, which is hereby incorporated by reference in its entirety.

GOVERNMENT FUNDING

This invention was made with government support under DA030316 awarded by the National Institutes of Health. The government has certain rights in the invention.

BACKGROUND

The prototypical analgesic, morphine, is widely employed clinically. It is generally recognized that morphine and a majority of structurally related analgesics mediate their action via mu opioid receptors (MOR). In this regard, the use of morphine and other mu-selective analgesics is problematic in the treatment of chronic inflammatory pain due to adverse effects that develop with chronic use.[1]

As members of the class A group of G protein-coupled receptors (GPCRs), three of the four members of the opioid receptor family mu (MOR), delta (DOR), and kappa (KOR) are activated by both the endogenous opioid peptide family and opiate structures related to morphine.[2]

The existence of opioid receptor heteromers in cultured cells,[3] and possibly in vivo, has offered new approaches to development of analgesics for the treatment of chronic pain without attendant side effects. As it is known that tolerance and/or dependence to chronic morphine treatment can be eliminated either by blocking DOR with a delta antagonist[4] or blocking DOR biosynthesis,[5,6] these studies are consistent with the MOR-DOR heteromer as a target for the mediation of these effects. Subsequent reports suggested that tolerance and dependence of mu opioid analgesics are likely due to targeting of MOR-DOR heteromer rather than a MOR homomer.[7,8] Thus, differences in signaling and trafficking pathways between the MOR-DOR heteromer and MOR homomer may contribute to the absence of tolerance and physical dependence in mice devoid of functional DOR.[9,10]

An approach based on the results of the above studies led to the development of a bivalent ligand (MDAN-21) that contains mu agonist and delta antagonist pharmacophores, produced potent antinociception in mice without tolerance or dependence.[11] It is noteworthy that the bridging of protomers by MDAN-21 was found to prevent internalization of MOR and DOR.[12]

There are a number of reports that opioid ligands targeting heteromers other than MOR-DOR do not display the same adverse effect profiles as morphine. For example, chronic administration of NNTA,[13] an opioid agonist that is selective for MOR-KOR heteromer, exhibits no tolerance or dependence. Similarly, INTA, a ligand that preferentially activates both MOR-KOR and DOR-KOR also is devoid of these side effects.[14] Additionally, the aversive effect generally associated with kappa agonists is greatly diminished with NNTA and totally eliminated with INTA, suggesting that it is the combination of protomers in the heteromer that governs the nature and intensity of the adverse effects.

Based on reports on the role of beta-arrestin in agonist-induced biasing of GPCRs,[15] it has been suggested that alteration or inhibition of recruitment of this scaffolding protein by the heteromer following activation may afford biased signaling pathways that could lead either to diminution or enhancement of adverse effects that would depend on the constitution of both the agonist and the heteromer.

The design and antinociceptive activity of a bivalent ligand (MMG22)[16] which contains both mu opioid agonist and metabotropic glutamate receptor-5 antagonist (mGluR$_5$) pharmacophores has been reported. As an opioid agonist that targets the MOR-mGluR$_5$ heteromer, MMG22 is both exceptionally potent and devoid of adverse effects upon chronic spinal administration to mice with inflammatory pain. Significantly, MMG22 is nearly 40,000-fold more potent than a co-administered mixture of monovalent mu agonist and mGluR$_5$ antagonist. Thus, a bivalent ligand capable of bridging the protomers of a heteromer is vastly superior to monovalent ligands. Some possibilities that could contribute to the phenomenal potency could include changes in trafficking and lack of tolerance. Subsequent studies on mice with fibrsarcoma revealed that the antinociception of MMG22 became more potent with cancer progression and, 21 days after implantation, MMG22 was 2.6 million-times more potent than morphine.[17]

Given the unusually high potency of MMG22 in targeting the MOR-mGluR$_5$ heteromer and absence of adverse effects, a similar approach for targeting a putative MOR heteromer containing a CCR$_5$ protomer. CCR$_5$ is one of the ten known CC chemokine receptors in the class A family of GPCRs that is a member of the four subfamilies of chemokines (CC, CXC, CX$_3$C, XC).[18]

Inflammation promotes release of chemokines whose signaling has been implicated in the pathogenesis of neuroinflammatory processes, including neuropathic pain.[19] As MOR and CCR$_5$ are present in neurons, glia, and co-localized in pain processing areas,[20,23] it is possible that MOR-CCR$_5$ heteromer exists in vivo as well, in view of its presence in cultured cells.[24,25] Given that CCR$_5$ is expressed on immune cells that include microglia, and is an important co-receptor involved in HIV-1 entry into immune cells,[24] it has been an important target in the treatment of neuroAIDS.

Accordingly, there is a need for therapeutic agents that treat pain (e.g., chronic inflammatory pain, neuropathic pain and HIV-induced neuropathy).

SUMMARY OF INVENTION

One embodiment provides a compound of formula I:

A-L-B  I wherein:

A is a residue of A1 or A2:

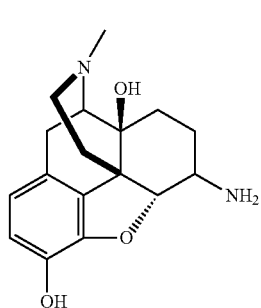

A1

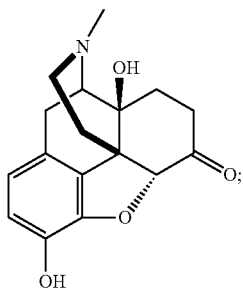

B is a residue of B1:

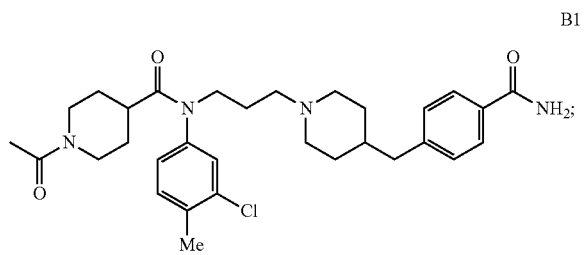 [SMILES: CC(=O)N1CCC(C(=O)N(CCCN2CCC(Cc3ccc(C(N)=O)cc3)CC2)c2ccc(C)c(Cl)c2)CC1]

and
L is a linker;
or a salt thereof.

One embodiment provides a pharmaceutical composition comprising a compound of formula I as described herein or a pharmaceutically acceptable salt thereof, and a pharmaceutically acceptable carrier.

One embodiment provides a method of treating pain (e.g., inflammatory pain, neuropathic pain, HIV-induced neuropathy) in an animal (e.g., a mammal such as a human) comprising administering to the animal in need thereof a compound of formula I or a pharmaceutically acceptable salt thereof as described herein.

One embodiment provides a compound of formula I or a pharmaceutically acceptable salt thereof as described herein for use in medical therapy.

One embodiment provides a compound of formula I or a pharmaceutically acceptable salt thereof as described herein for the prophylactic or therapeutic treatment of pain (e.g., inflammatory pain, neuropathic pain, HIV-induced neuropathy).

One embodiment provides the use of a compound of formula I or a pharmaceutically acceptable salt thereof as described herein to prepare a medicament for treating pain (e.g., inflammatory pain, neuropathic pain, HIV-induced neuropathy) in an animal (e.g., a mammal such as a human).

One embodiment provides processes and intermediates disclosed herein that are useful for preparing a compound of formula I or a salt thereof.

BRIEF DESCRIPTION OF FIGURES

FIG. 13 shows the effect of spacer length between pharmacophores on antinociception in LPS treated mice.

DETAILED DESCRIPTION

Figure 1A:
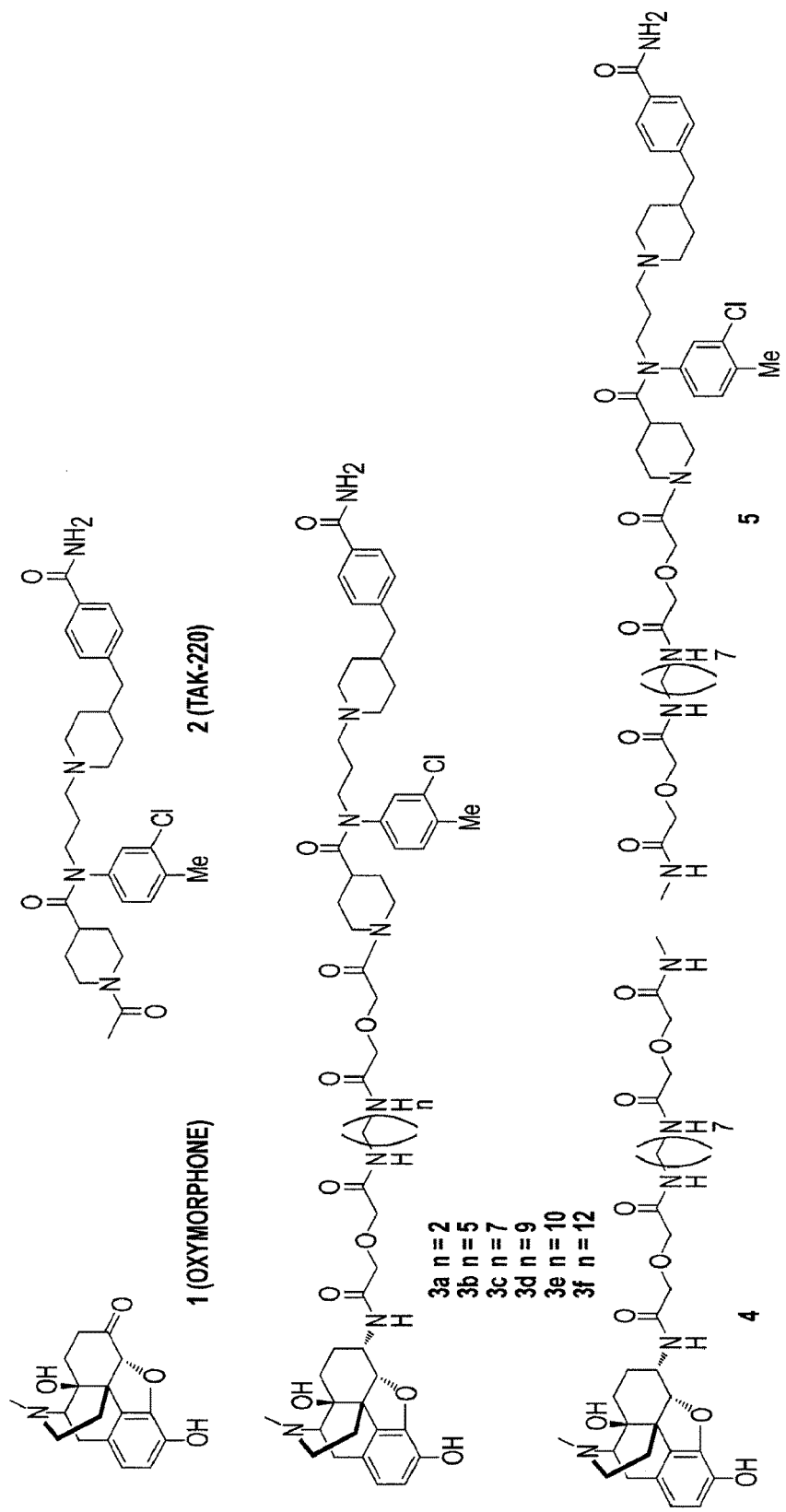
FIG. 1A shows the Mu opioid agonist, oxymorphone (1) and $CCR_5$ antagonist, TAK-220 (2) pharmacophores which have been incorporated into the bivalent ligand series (3a-3f) and monovalent ligands 4, and 5.

Described herein is the design, synthesis and biological evaluation of a bivalent compound having mu agonist and CCR$_5$ antagonist pharmacophores tethered through a linker (e.g., compounds of formula I). Compounds of formula I produce antinociception in inflamed mice, and the structure-activity relationship of the compounds implicates MOR-CCR$_5$ as the target. Described herein is a study of LPS-induced proinflammatory cytokine IL-6 secretion in murine primary microglia and the attenuation of IL-6 secretion with compounds of formula I. Furthermore, a combination of minocycline and a compound of formula I attenuated synergistically IL-6 secretion in the presence of LPS. Thus, compounds of formula I have potential for treatment of pain (e.g., chronic inflammatory pain, neuropathic pain and HIV-induced neuropathy).

The following definitions are used, unless otherwise described.

The term "halo" or "halogen" is fluoro, chloro, bromo, or iodo

The term "alkyl" is a straight or branched saturated hydrocarbon. For example, an alkyl group can have 1 to 8 carbon atoms (i.e., (C$_1$-C$_8$)alkyl) or 1 to 6 carbon atoms (i.e., (C$_1$-C$_6$) alkyl) or 1 to 4 carbon atoms.

The term "treatment" or "treating," to the extent it relates to a disease or condition includes inhibiting the disease or condition, eliminating the disease or condition, and/or relieving one or more symptoms of the disease or condition.

The term "patient" as used herein refers to any animal including mammals such as humans, higher non-human primates, rodents domestic and farm animals such as cow, horses, dogs and cats. In one embodiment, the patient is a human patient.

The phrase "therapeutically effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "residue" as it applies to the residue of a compound (e.g., a residue of A1, A1a, A2, B1) used herein refers to a compound (e.g., A1, A1a, A2, B1) that has been modified in any manner which results in the creation of an open valence wherein the site of the open valence is the site wherein the linker is attached to the compound. The open valence can be created by the removal of 1 or more atoms from the compound (e.g., removal of a single atom such as hydrogen or removal of more than one atom such as a group of atoms including but not limited to an amine, hydroxyl, methyl, amide (e.g., —C(=O)NH$_2$) or acetyl group). The open valence can also be created by the chemical conversion of a first function group of the compound to a second functional group of the compound (e.g., reduction of a carbonyl group, replacement of a carbonyl group with an amine,) followed by the removal of 1 or more atoms from the second functional group to create the open valence. The open valence can vary in location and number of atoms and thus provide a residue of A1/A1a/A2 joined to a residue of B1 by a linker to provide the compound of formula I.

The term linker as used herein includes any moiety that can be used to link A1/A2 to B1 to provide a compound of formula I which compound operates as described herein.

The compounds disclosed herein can also exist as tautomeric isomers in certain cases. Although only one delocalized resonance structure may be depicted, all such forms are contemplated within the scope of the invention.

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific embodiments listed below for radicals, substituents, and ranges, are for illustration only; they do not exclude other defined embodiments or values or other values within defined ranges for the radicals and substituents. It is to be understood that two or more embodiments may be combined. Specific embodiments listed below are embodiments for compounds of formula I as well as all related formulas (e.g., compounds of formulas Ia, Ib).

In one embodiment A is a residue of A1.

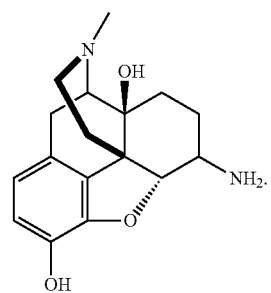

A1

In one embodiment A is a residue of A1a:

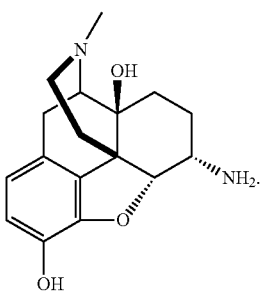

A1a

In one embodiment A is:

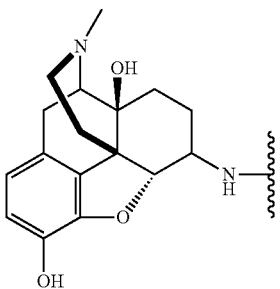

which compound is a residue of A1.

In one embodiment A is:

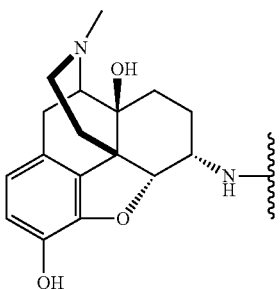

which compound is a residue of A1a.

In one embodiment the residue of A1, A2 or A1a is derivable by the removal of one or more atoms from A1, A2 or A1a.

In one embodiment the residue of A1, A2 or A1a is derivable by the removal of 1, 2, 3 or 4 atoms from A1, A2 or A1a.

In one embodiment the residue of A1, A2 or A1a is derivable by the removal of 1, 2, 3, 4, 5 or 6 atoms from A1, A2 or A1a.

In one embodiment the residue of A1, A2 or A1a is derivable by the removal of one atom from A1, A2 or A1a.

In one embodiment the residue of A1, A2 or A1a is derivable by the removal of a hydrogen from A1, A2 or A1a.

In one embodiment the residue of A1, A2 or A1a is derivable by the removal of a hydrogen from a heteroatom or an alkyl group of A1, A2 or A1a.

In one embodiment the residue of A1, A2 or A1a is derivable by the removal of a hydrogen from a heteroatom of A1, A2 or A1a.

In one embodiment the residue of A1 or A1a is derivable by the removal of a hydrogen from the —NH$_2$ group of A1 or A1a.

In one embodiment the residue of B1 is derivable by the removal of one or more atoms from B1.

In one embodiment the residue of B1 is derivable by the removal of 1, 2, 3 or 4 atoms from B1.

In one embodiment the residue of B1 is derivable by the removal of 1, 2, 3, 4, 5 or 6 atoms from B1.

In one embodiment the residue of B1 is derivable by the removal of one atom from B1.

In one embodiment the residue of B1 is derivable by the removal of a hydrogen from B1.

In one embodiment the residue of B1 is derivable by the removal of a hydrogen from a heteroatom or an alkyl group of B1.

In one embodiment the residue of B1 is derivable by the removal of a hydrogen from an alkyl group of B1.

In one embodiment the residue of B1 is derivable by the removal of a hydrogen from the —C(=O)CH$_3$ group of B1.

In one embodiment compounds of formula I are compounds of formula Ia:

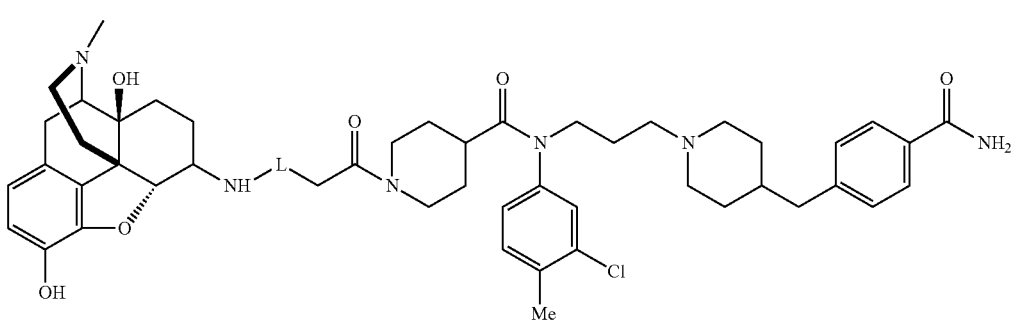

Ia or a salt thereof.

In one embodiment compounds of formula I are compounds of formula Ib:

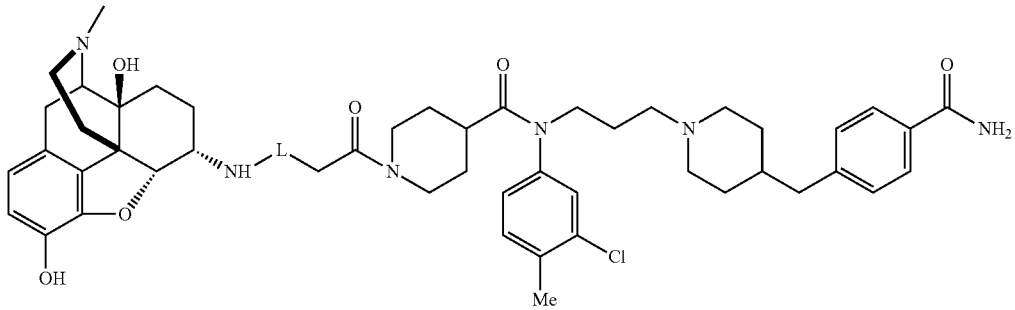

or a salt thereof.

In one embodiment the linker comprises about 5 to about 100 atoms.

In one embodiment the linker comprises about 5 to about 80 atoms.

In one embodiment the linker comprises about 5 to about 60 atoms.

In one embodiment the linker comprises about 15 to about 100 atoms.

In one embodiment the linker comprises about 15 to about 80 atoms.

In one embodiment the linker comprises about 15 to about 60 atoms.

In one embodiment the linker of any of the above six embodiments comprises atoms selected from halo, C, O, N and S. It is to be understood that the open valences of any of the C, O, N and S atoms are hydrogen. In one embodiment the linker of any of the above six embodiments comprises atoms selected from C, O, N and S. It is to be understood that the open valences of any of the C, O, N and S atoms are hydrogen.

In one embodiment the linker comprises about 15 to about 300 atoms.

In one embodiment the linker comprises about 15 to about 240 atoms.

In one embodiment the linker comprises about 15 to about 180 atoms.

In one embodiment the linker comprises about 45 to about 300 atoms.

In one embodiment the linker comprises about 45 to about 240 atoms.

In one embodiment the linker comprises about 45 to about 180 atoms.

In one embodiment the linker of any of the above six embodiments comprises atoms selected from H, halo, C, O, N and S. In one embodiment the linker of any of the above six embodiments comprises atoms selected from H, C, O, N and S.

In one embodiment the linker comprises groups selected from unbranched chains, branched chains and cyclic groups.

In one embodiment the linker comprises groups selected from unbranched chains and branched chains.

In one embodiment the linker consists of groups selected from unbranched chains and branched chains.

In one embodiment the linker is a ($C_6$-$C_{50}$) saturated or unsaturated hydrocarbon chain which chain is branched or unbranched, wherein one or more of the carbon atoms of the chain is replaced by a carbonyl, thiocarbonyl, O, N or S.

In one embodiment the linker is a ($C_{10}$-$C_{30}$) saturated or unsaturated hydrocarbon chain which chain is branched or unbranched, wherein one or more of the carbon atoms of the chain is replaced by a carbonyl, thiocarbonyl, O, N or S.

In one embodiment the linker is represented by formula II:

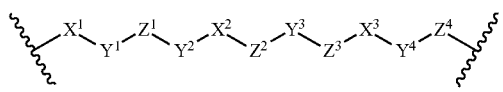

wherein:

$X^1$ is

or absent;
$Y^1$ is ($C_1$-$C_6$)alkyl;
$Z^1$ is O, $NR^a$ or absent;
$Y^2$ is ($C_1$-$C_6$)alkyl;
$X^2$ is

or absent;
$Z^2$ is O, $NR^a$ or absent;
$Y^3$ is ($C_1$-$C_{20}$)alkyl;
$Z^3$ is O, $NR^a$ or absent;
$X^3$ is

or absent;
$Y^4$ is ($C_1$-$C_6$)alkyl;
$Z^4$ is O, $NR^a$ or absent; and
each $R^a$ is independently H or ($C_1$-$C_6$)alkyl.

In one embodiment $X^1$, $X^2$ and $X^3$ are each

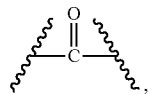

In one embodiment $Z^1$ and $Z^4$ are each O.
In one embodiment $Z^2$ and $Z^3$ are each NH.
In one embodiment $Y^1$, $Y^2$ and $Y^4$ are each independently $(C_1-C_3)$alkyl.
In one embodiment $Y^3$ is $(C_2-C_{10})$alkyl.
In one embodiment the linker is:

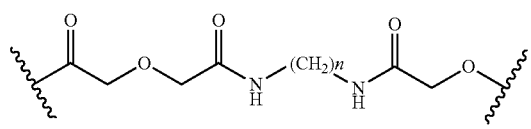

wherein n is 2, 5, 7 or 10

In one embodiment the linker is:

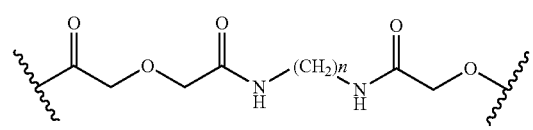

wherein n is 2, 5, 7, 9 or 10.
In one embodiment the linker is:

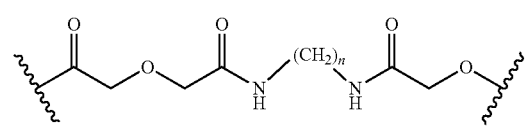

wherein n is 2, 5, 7, 9, 10 or 12.
In one embodiment a compound of formula I is:

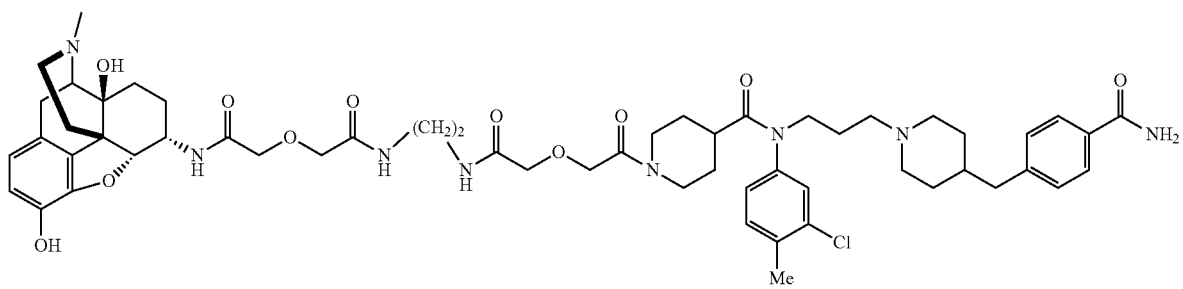

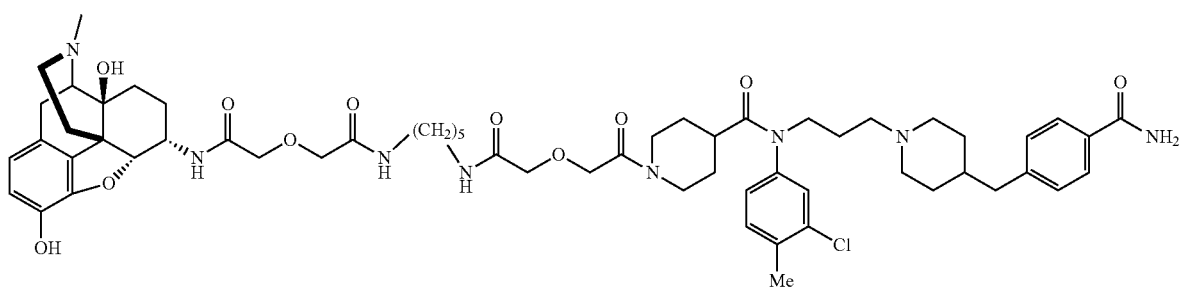

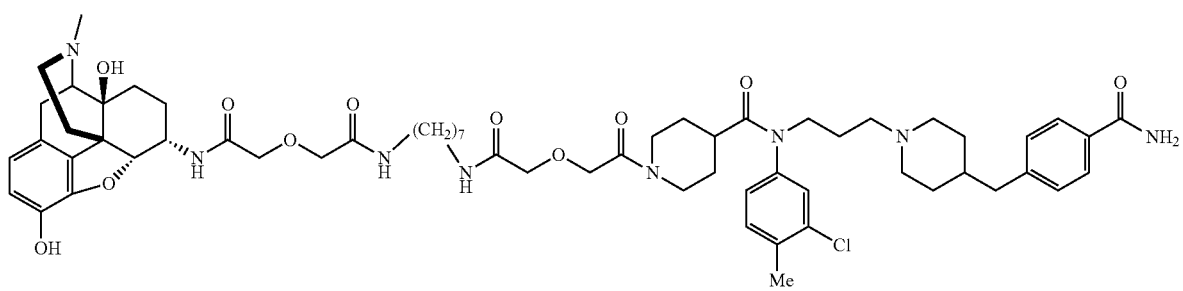

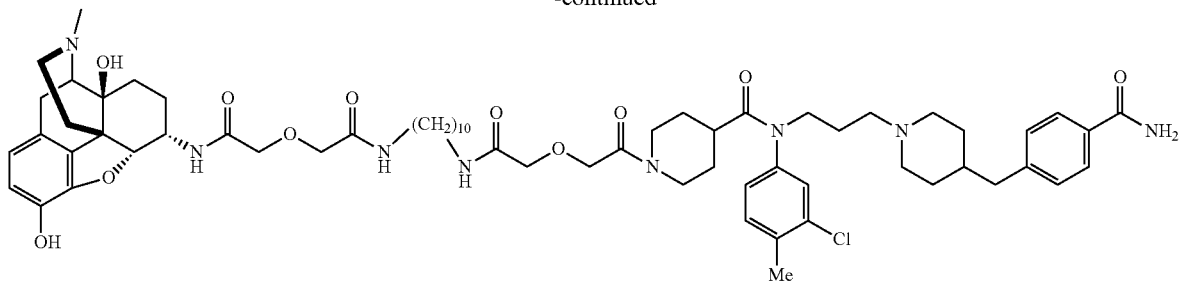

or a salt thereof.

In one embodiment a compound of formula I is:

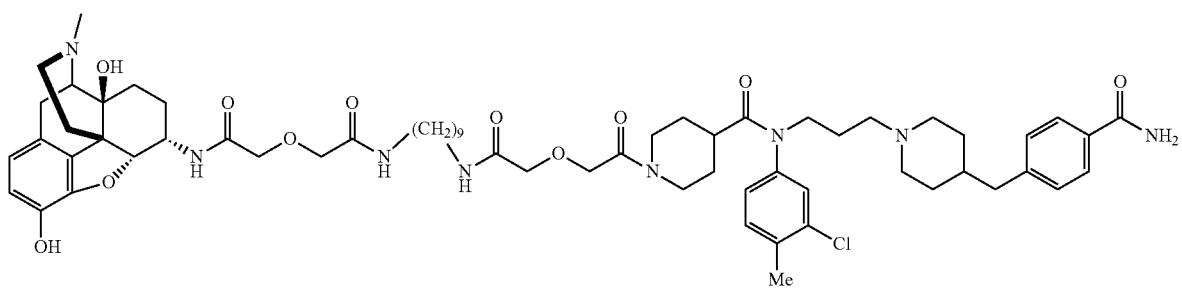

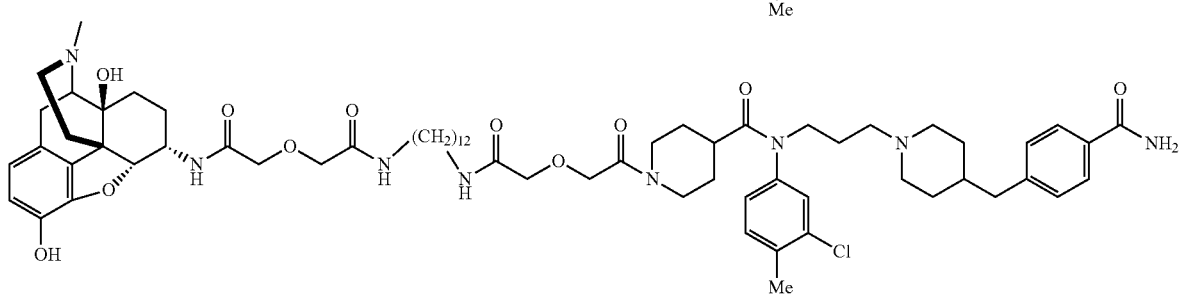

or a salt thereof.

In one embodiment a salt is a pharmaceutically acceptable salt.

Processes for preparing compounds of formula I are provided as embodiments of the invention.

The compounds of formula I (or salts thereof) described herein are useful for treating pain in an animal (e.g., a mammal such as a human including a human patient). Pain as used herein includes all type of pain such as but not limited to inflammatory pain (e.g., chronic inflammatory pain), neuropathic pain and pain due to diseases such as sickle cell anemia. Neuropathic pain includes but is not limited to pain that is caused or induced by disease (e.g., diabetes (diabetic neuropathy), HIV, cancer, neurodegenerative disease), drug use (e.g., such as drugs to treat cancer including cisplatin-(cisplatin induced neuropathy)) and trauma (e.g., spinal injury). In one embodiment the pain is inflammatory pain (e.g., chronic inflammatory pain), or neuropathic pain. In one embodiment the neuropathic pain is associated or induced by disease, trauma or drug use. In one embodiment the neuropathic pain is associated or induced by sickle cell anemia, diabetes, HIV, cancer, neurodegenerative disease, drug use. In one embodiment the neuropathic pain is associated or induced by drug use. In one embodiment the neuropathic pain is associated or induced by trauma (e.g., spinal injury).

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts include organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic acid addition salts may also be formed, which include a physiological acceptable anion, for example, chloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In some embodiments, one or more of the compounds disclosed herein are co-administered with one or more other active therapeutic agents. Co-administration of a compound disclosed herein with one or more other active therapeutic agents generally refers to simultaneous or sequential administration of a compound disclosed herein and one or more other active therapeutic agents, such that therapeutically effective amounts of the compounds disclosed herein and one or more other active therapeutic agents are both present in the body of the patient.

In some embodiments, one or more of the compounds disclosed herein are co-administered with one or more active therapeutic agents by combining the compounds disclosed herein with the other therapeutic agents in a unitary dosage form for simultaneous or sequential administration to a patient. Thus, this combination therapy may be administered as a simultaneous or sequential regimen. When administered sequentially, the combination may be administered in two or more administrations.

The invention will now be illustrated by the following non-limiting Examples.

Example 1

Design Rationale of Ligands

Figure 6:
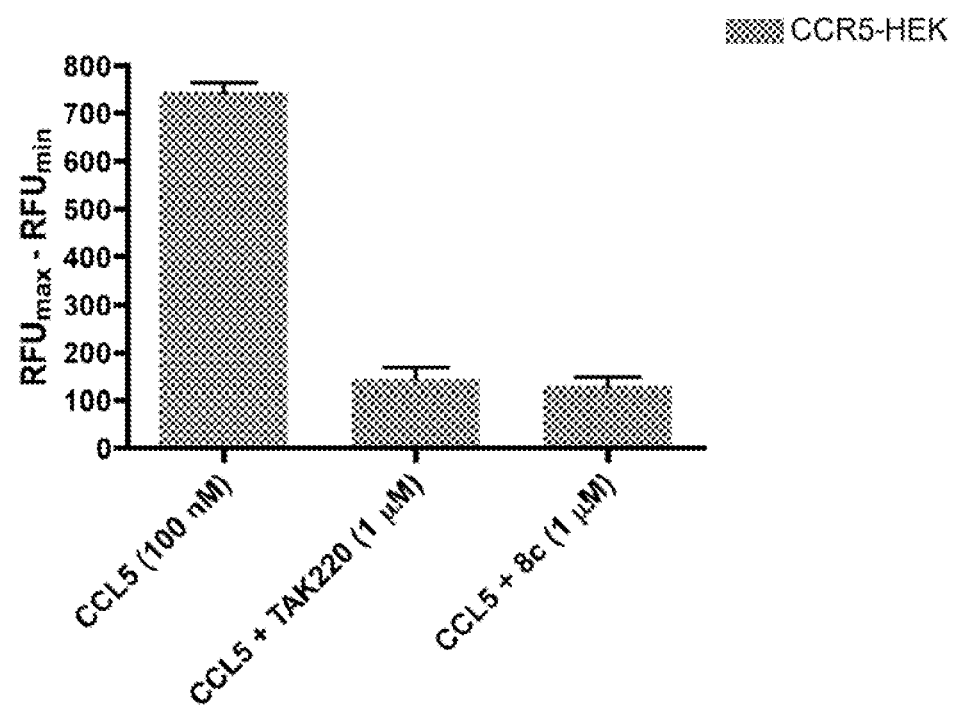
FIG. 6 shows $CCl_5$ stimulation of $CCR_5$ receptors expressed in HEK-293 cells; inhibition of $Ca^{2+}$ by TAK-220 and TAK-220 derivative 8c with a short space.

The pharmacophores for targeting MOR-CCR$_5$ heteromer are derived from the agonist oxymorphone (1)[25] and CCR$_5$ antagonist TAK-220[26] (2). Oxymorphone has been employed as precursor for the mu opioid agonist pharmacophore in the synthesis of other bivalent ligands.[16,27-29] The utility of TAK-220 as a building partner was verified by attaching a short spacer to the pharmacophore and evaluating its ability to antagonize CCL$_5$-stimulated CCR$_5$ receptors expressed in HEK293 cells, as illustrated in FIG. 6. The TAK-220 derivative was as effective as TAK-220 in inhibiting CCR$_5$. With that information, members of the MCC (3a-3f) series having different length spacers (14 to 24 atoms) were synthesized. The compounds include the compound MCC22 (3e). The selection of spacer lengths were based on prior studies that revealed a range of approximately 18-22 atoms for effective bridging of GPCR protomers.[11,27,30-33] In addition, the monovalent ligands 4[11] and 5 as controls (FIG. 1) were prepared.

Methods

A. Chemistry

Ligand Design and Synthesis.

Figure 5:
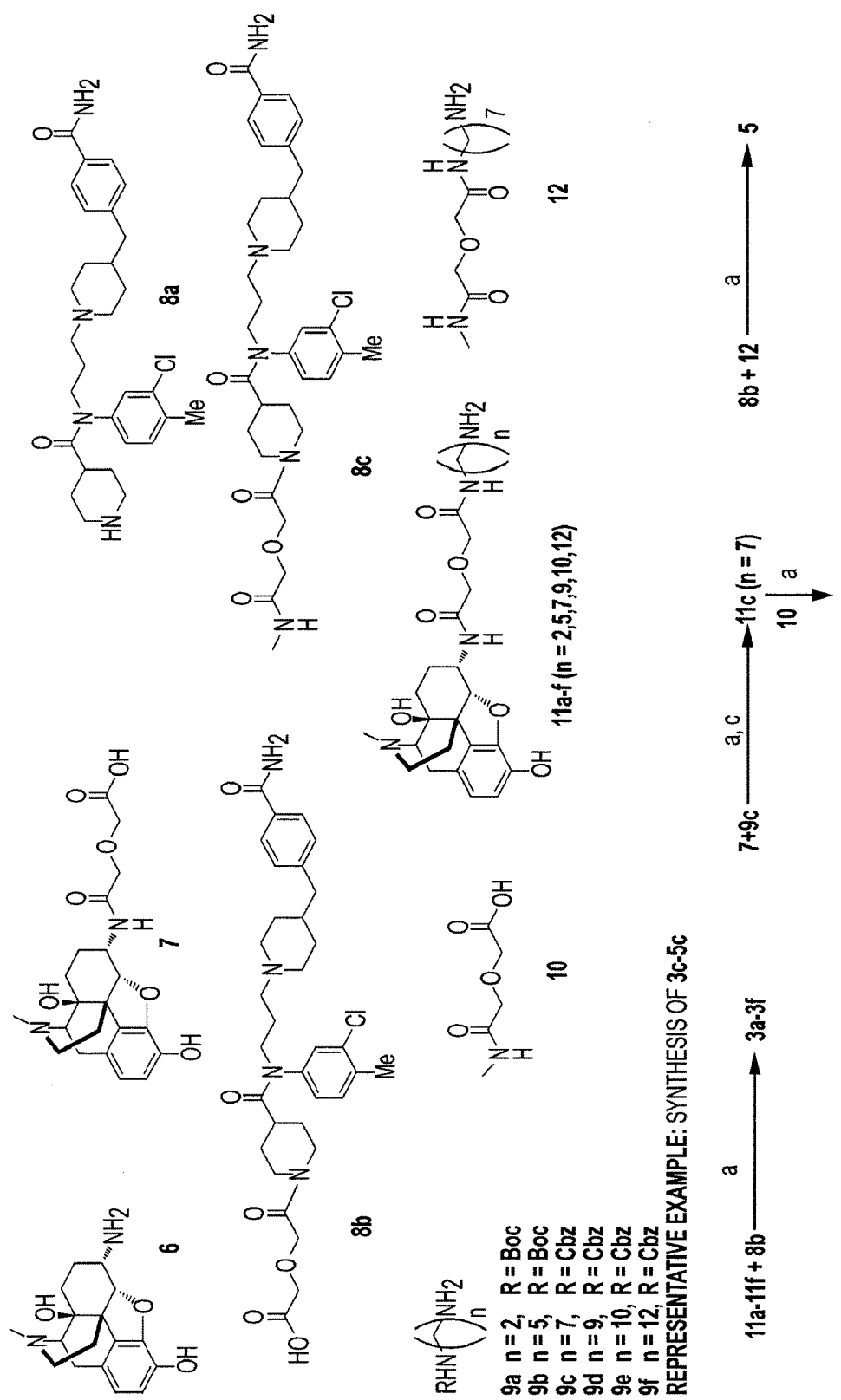
FIG. 5 shows the intermediates employed in the synthesis of bivalent ligands 3a-3f and monovalents 4 and 5.

The bivalent series 3a-3f (FIG. 1) in the present study contain pharmacophores derived from the mu opioid agonist, oxymorphone (1), and the CCR$_5$ antagonist, TAK-220 (2).[62] Their synthesis started with the elaboration of intermediates depicted in FIG. 5. With the exception of 8a-8c, the intermediates 7-12 have been reported by us previously.[16,28,29,63] Using the procedure of a literature reference,[62] the amine 8a was prepared and converted into 8c. Calcium mobilization studies in CCR$_5$ expressing HEK cells stimulated by CCL$_5$ revealed that 8c was equally potent at inhibiting calcium release (FIG. 6). Therefore, 8b was prepared from 8a by its reaction with glycolic anhydride and used for preparation of ligands 3a-3f and 5. Finally, the intermediates were linked using standard HOBt/DCC coupling procedure as shown for the synthesis of 3c, 5, and 11c in FIG. 5.

Chemical Synthesis (General Chemistry).

Oxymorphone was obtained from Mallinckrodt & Co. All other chemicals and solvents were purchased from Aldrich or Fisher without further purification. $^1$H and $^{13}$C NMR spectroscopy were obtained on 300 MHz on an Oxford Varian VXR 300 MHz NMR Spectrometer. Mass spectroscopy was obtained on Bruker BioTOF II mass spectrometry. Synthesis of CCR$_5$ antagonist 2, monovalent 4, intermediates 6, 7, 9a-9f, 10, 11a-11e have been previously reported. Purities of bivalent ligands (3a-3f), and the monovalent ligands (4, 5 and 8c) were over 98% based on analysis on HPLC column (Phenomenex Luna SB-C18 (2) 5u 4.6×250 mm) which was eluted with MeOH/Buffer (60:40) at a flow rate of 1 ml/min.

Chemical Synthesis (General procedure for the synthesis of Bivalent ligands 3a-3f). Carboxylic acid 8b (0.97 mmol) was activated with HOBt.H$_2$O (0.74 mmol), DIPEA (168.4 µL, 0.97 mmol), DMAP (9.1 mg, 0.074 mmol) and EDCI (185.4 mg, 0.97 mmol) in DMF (0.5 mL) at 0° C. under N$_2$ atmosphere for 10 min. The requisite amine 11a-11f (0.74 mmol) in DMF (2 mL) was added to the above mixture and stirred under N$_2$ atmosphere at room temperature overnight. The reaction mixture was evaporated in vacuum. The residue was purified by column chromatography on silica gel [CH$_2$Cl$_2$/MeOH/NH$_4$OH=95:4:1 to 92:7.5:0.5 to 89:10:1; (v/v/v)] to give the objective compounds.

Synthesis of N-(3-(4-(4-carbamoylbenzyl)piperidin-1-yl)propyl)-N-(3-chloro-4-methylphenyl)-1-(19-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-5,15,19-trioxo-3,17-dioxa-6,14-diazanonadecan-1-oyl)piperidine-4-carboxamide, MCC19 (3c)

To the mixture of acid 8b (0.040 g, 0.064 mmol, 1.1 equ) is added HBTU (0.045 g, 0.117 mmol, 2.0 equ) and HOBt solution (0.235 mL of 0.5M HOBt solution in DMF, 0.117 mmol, 2.0 equ) at r.t and stirred for 15 min. A clear colorless solution with no precipitate resulted. Added in a solution of amine 11c (0.031 g, 0.0584 mmol, 1.0 equ) which was pre-neutralized with DIPEA (0.025 mL, 0.02 g, 0.117 mmol, 2.25 equ)) in DMF (2.5 mL). The reaction was allowed to stir at r.t for 18 hrs. The solvent was removed in vacuum and further purification was performed over silica gel column chromatography using 95:4:1 to 92:7.5:0.5 to 89:10:1 CH$_2$Cl$_2$:MeOH:NH$_4$OH (v:v:v). The final product 3c was isolated as white solid (0.032 g, 48% yield).

$^1$H NMR (400 MHz, CDCl$_3$) δ 7.73 (d, 7.2 Hz, 2H), 7.17-7.19 (m, 4H), 6.95-6.98 (m, 2H), 6.71 (d, 8 Hz, 1H), 6.51 (d, 8 Hz, 1H), 5.92 (br s, 1H), 4.56 (br s, 1H), 4.43 (br d, 11.2 Hz, 1H), 4.22-4.24 (m, 3H), 3.99-4.07 (m, 4H), 3.82 (br d, 12.8 Hz, 1H), 3.55 (br s, 1H), 3.62 (t, 8 Hz, 2H), 3.37-3.31 (m, 3H), 3.10 (br d, 18.4 Hz, 1H), 2.94 (d, 3H), 2.71-2.87 (m, 4H), 2.54-2.60 (m, 3H), 2.25-2.41 (m, 3H), 2.42 (s, 3H), 2.34 (s, 3H), 1.17-1.90 (m, 27H).

$^{13}$C NMR (100 MHz) δ 173.80, 169.42, 169.31, 169.19, 168.66, 167.01, 145.67, 145.00, 140.75, 138.23, 136.46, 135.16, 131.98, 130.92, 130.64, 128.22, 128.37, 127.37, 126.29, 125.17, 119.21, 117.90, 89.36, 71.56, 71.39, 71.24, 69.64, 68.99, 64.55, 55.82, 53.72, 50.93, 47.87, 46.35, 45.67, 44.78, 43.91, 43.49, 43.04, 42.85, 40.50, 39.16, 38.94, 38.62, 37.51, 35.98, 35.36, 33.24, 31.84, 28.94, 28.86, 28.30, 28.10, 26.38, 26.20, 25.09, 22.04, 21.11, 19.45.

MS(ESI)-TOF observed 1139.5122 (M+1), 1161.5122 (M+Na$^+$), required exact mass 1138.5870.

Synthesis of N-((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)-2-(3,7,17-trioxo-5-oxa-2,8,16-triazaoctadecan-18-yl)oxy)acetamide (4)

The synthesis of compound 4 was reported previously.[11]

Synthesis of N-(3-(4-(4-carbamoylbenzyl)piperidin-1-yl)propyl)-N-(3-chloro-4-methylphenyl)-1-(3,7,17-trioxo-5,19-dioxa-2,8,16-triazahenicosan-21-oyl)piperidine-4-carboxamide (5)

To the mixture of acid 8b (0.128 g, 0.204 mmol, 1.1 equ) is added HBTU (0.141 g, 0.37 mmol, 2.0 equ) and HOBt solution (0.75 mL of 0.5M HOBt solution in DMF, 0.37 mmol, 2.0 equ) at r.t and stirred for 15 min. A clear colorless solution with no precipitate resulted. Added in a solution of amine 12 (0.055 g, 0.18 mmol, 1.0 equ) which was pre-neutralized with DIPEA (0.105 mL, 0.077 g, 0.59 mmol, 3.20 equ)) in DMF (2.0 mL). The reaction was allowed to stir at r.t for 48 hrs. The solvent was removed in vacuo and further purification was performed over silica gel column chromatography using 97:2.5:0.5 to 95:4:1 to 92:7.5:0.5 to 89:10:1 DCM:MeOH:Ammonium Hydroxide. The final product 5 was isolated as off-white solid (0.06 g, 37% yield).

$^1$H NMR (400 MHz, CDCl$_3$) δ 7.74 (d, 8 Hz, 2H), 7.51 (d, 8 Hz, 2H), 7.20 (s, 1H), 7.18 (s, 2H), 6.45 (br s, 1H), 4.18-4.30 (m, 2H), 4.04 (s, 2H), 4.02 (s, 2H), 4.00-4.10 (m, 2H), 3.42 (t, 7 Hz, 2H), 3.57 (d, 12 Hz, 1H), 3.25 (m, 2H), 2.79-2.96 (m, 2H), 2.80 (br d, 16 Hz, 3H, methyl on amide nitrogen), 2.57 (d, 6.4 Hz, 2H), 2.30-2.50 (4H), 2.41 (s, 3H, methyl on aromatic ring), 1.85-2.00 (m, 2H), 1.40-1.80 (m, 14H), 1.24-1.38 (m, 10H).

$^{13}$C NMR (100 MHz, CDCl$_3$) δ 173.68, 169.35, 169.25, 169.21, 168.47, 166.88, 144.86, 140.65, 136.63, 135.26, 131.95, 130.99, 129.25, 128.36, 127.37, 126.28, 71.68, 71.09, 71.06, 69.62, 55.70, 53.67, 43.51, 42.78, 41.09, 38.95, 38.75, 37.40, 31.64, 29.22, 29.12, 28.64, 28.53, 28.11, 26.53, 26.43, 25.67, 24.99, 24.95, 19.74.

MS(ESI)-TOF observed 868.4800 (M+1), 890.4615 (M+Na$^+$), required exact mass 867.4661.

Synthesis of N-(3-(4-(4-carbamoylbenzyl)piperidin-1-yl)propyl)-N-(3-chloro-4-methylphenyl)piperidine-4-carboxamide (8a)

The precursor amine tert-butyl 4-((3-(4-(4-carboxybenzyl)piperidin-1-yl)propyl)(3-chloro-4-methylphenyl)carbamoyl)piperidine-1-carboxylate was prepared as yellow oil by elaboration of original procedure of TAK-220. To a cold (5° C.) solution of this Boc protected amine (1.130 g, 1.847 mmol, 1.0 equ) in 20 mL CH$_2$Cl$_2$ is added trifluroacetic acid (TFA) (2.14 mL, 3.16 g, 27.70 mmol, 15.0 equ) dropwise. The reaction was allowed to warm to room temperature and stirred 18 hrs. when TLC indicated completion of reaction. The light yellow solution is concentrated in vacuo followed by azeotropic distillation from toluene (3×50 mL) and trituration with pentane/DCM provided TFA salt as amorphous solid. In order to obtain un-protected piperidine, the TFA salt was dissolved in 15 mL water and slowly basified to pH 9-10 with ammonium hydroxide (30%, ~15 mL used). The aqueous solution then extracted with CH$_2$Cl$_2$, dried (MgSO$_4$), filtered, concentrated in vacuo to provide crude product. The aqueous layer is brought to pH=7 and rigorously extracted with EtOAc, dried (MgSO$_4$), filtered, concentrated in vacuo to provide more crude product. The combined crude product was further purified on SiO$_2$ column chromatography (pre-treated with 1% TEA) using EtOAc: MeOH (10:0 to 9:1 to 8:2 to 7:3, all with 1% TEA) as eluent to give 0.76 g (81%) of un-protected piperidine 8a as light yellow oil.

$^1$H NMR (400 MHz, CD$_3$OD) δ 7.78 (d, 8 Hz, 2H), 7.41 (m, 2H), 7.24 (d, 8 Hz, 2H), 7.15 (d, 8 Hz, 1H), 3.66 (t, 7 Hz, 2H), 3.31 (t, 1.6 Hz, 2H), 3.15 (d, 12 Hz, 2H), 2.92 (d, 12 Hz, 2H), 2.35-2.61 (m, 7H), 2.41 (s, 3H), 1.96 (t, 12 Hz, 2H), 1.61-1.80 (m, 9H), 1.25-1.33 (m, 2H.

$^{13}$C NMR (100 MHz, CD$_3$OD) δ 180.29, 172.77, 172.72, 146.06, 142.06, 137.82, 136.14, 133.30, 132.58, 130.22, 129.66, 128.69, 127.97, 56.84, 54.62, 44.83, 43.61, 39.76, 38.63, 35.24, 32.50, 28.30, 25.64, 24.28, 22.58, 19.80, 14.75.

MS(ESI)-TOF observed 511.2465 (M+1), required exact mass 510.2762.

Synthesis of 2-(2-(4-((3-(4-(4-carbamoylbenzyl)piperidin-1-yl)propyl)(3-chloro-4-methylphenyl)carbamoyl)piperidin-1-yl)-2-oxoethoxy)acetic acid (8b)

To a mixture of commercially available glycolic anhydride (0.088 g, 0.737 mmol, 1.0 equ) and piperidine 8a (0.380 g, 0.737 mmol, 1.0 equ) at room temperature is added THF (7 mL). The reaction was allowed to stir for 18 hrs. The solvent was removed to provide 8b as a white solid (0.462 g, 100% yield).

MS(ESI)-TOF observed 625.4160 (M−1) (negative mode), 627.3378 (M+1), 649.3180 (M+Na) (positive mode); required exact mass 626.2871.

Synthesis of N-(3-(4-(4-carbamoylbenzyl)piperidin-1-yl)propyl)-N-(3-chloro-4-methylphenyl)-1-(2-(2-(methylamino)-2-oxoethoxy)acetyl)piperidine-4-carboxyamide (8c)

The target compound was obtained by reaction of 8b with commercially available methylamine as described for monovalent 5.

Yield: >90%

$^1$H NMR (400 MHz, CD$_3$OD) δ 7.78 (d, 8 Hz, 2H), 7.41 (m, 2H), 7.23 (d, 8 Hz, 2H), 7.16 (d, 8 Hz, 1H), 4.22-4.42 (m, 3H), 4.0 (s, 2H), 3.66 (m, 3H), 3.33-3.34 (m, 2H), 2.86 (d, 7.2 Hz, 2H), 2.76 (s, 4H), 2.57 (d, 6.4 Hz, 2H), 2.42-2.48 (m, 2H), 2.40 (s, 3H), 2.31 (t, 8 Hz, 2H), 1.90 (t, 12 Hz, 2H), 1.58-1.73 (m, 9H), 1.22-1.30 (m, 2H).

$^{13}$C NMR (100 MHz, CD$_3$OD) δ 175.97, 172.39, 172.12, 169.24, 146.15, 142.09, 137.85, 136.16, 133.30, 132.56, 130.24, 129.68, 128.67, 127.98, 71.44, 70.09, 56.94, 54.71, 44.65, 43.65, 42.09, 40.68, 38.74, 32.62, 29.74, 29.22, 25.80, 25.74, 19.79.

MS(ESI)-TOF observed 640.3807 (M+1), 662.3631 (M+Na) (positive mode); required exact mass 639.3187.

Synthesis of N-(3-(4-(4-carbamoylbenzyl)piperidin-1-yl)propyl)-N-(3-chloro-4-methylphenyl)-1-(14-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-5,10,14-trioxo-3,12-dioxa-6,9-diazatetradecan-1-oyl)piperidine-4-carboxamide, MCC14 (3a)

Yield: ~100%, off-white amorphous solid $^1$H NMR (400 MHz, CDCl$_3$) δ 7.74 (d, 7.6 Hz, 2H), 7.28-7.29 (m, 1H), 7.17-7.19 (m, 3H), 6.96 (d, 8.0 Hz, 1H), 6.71 (d, 8.0 Hz, 1H), 6.51 (d, 8.0 Hz, 1H), 4.53-4.60 (m, 2H), 4.42 (d, 12.8 Hz, 1H), 4.18-4.28 (m, 2H), 3.99-4.04 (m, 6H), 3.63 (t, 7.2 Hz, 2H), 3.40-3.54 (m, 5H), 3.12 (br d, 18.4 Hz, 1H), 2.84 (d, 10.4 Hz, 2H), 2.77 (d, 6.4 Hz, 2H), 2.59 (d, 6.8 Hz, 1H), 2.55 (6.4 Hz, 2H), 2.19-2.24 (m, 7H), 2.39 (s, 3H), 2.34 (s, 3H), 1.83 (t, 11.2 Hz, 2H), 1.53-1.79 (m, 13H), 1.36-11.42 (m, 1H), 1.21-1.30 (m, 3H), 0.79-1.08 (m, 1H).

$^{13}$C NMR (100 MHz) δ 173.46, 171.25, 169.35, 169.18, 167.82, 167.24, 145.55, 145.00, 140.76, 138.16, 136.56, 135.23, 131.97, 130.99, 130.80, 129.23, 128.41, 127.36, 126.29, 125.24, 119.23, 117.58, 89.23, 71.50, 71.08, 70.80, 69.62, 69.58, 64.60, 55.88, 53.83, 48.04, 46.38, 45.68, 45.58, 44.85, 43.53, 43.08, 42.92, 41.21, 39.57, 38.87, 38.55, 38.40, 37.64, 33.21, 31.94, 29.04, 28.58, 28.10, 25.21, 22.04, 21.20, 19.76.

MS (ESI): m/z Observed 1069.9 (M+1); 1069.5, Calculated for C$_{56}$H$_{73}$ClN$_8$O$_{11}$[M+1]$^+$.

Synthesis of N-(3-(4-(4-carbamoylbenzyl)piperidin-1-yl)propyl)-N-(3-chloro-4-methylphenyl)-1-(17-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-5,13,17-trioxo-3,15-dioxa-6,12-diazaheptadecan-1-oyl)piperidine-4-carboxamide, MCC17 (3b)

Yield: 73%, white solid.

$^1$H NMR (400 MHz, CDCl$_3$) δ 7.73 (d, 6.4 Hz, 2H), 7.40-7.50 (m, 1H), 7.27-7.29 (m, 1H), 7.17-7.20 (m, 3H), 6.95-7.00 (m, 2H), 6.71 (d, 8.0 Hz, 1H), 6.52 (d, 8.0 Hz, 1H), 6.43 (br s, 1H), 5.87 (br s, 1H), 4.50-4.60 (m, 2H), 4.43 (br d, 128 Hz, 1H), 4.23-4.28 (m, 2H), 3.98-4.08 (m, 5H), 3.63 (t, 7.2 Hz, 2H), 3.23-3.31 (m, 5H), 3.12 (br d, 18.4 Hz, 1H), 2.94-2.96 (m, 1H), 2.84 (d, 10.4 Hz, 2H), 2.77 (d, 6.4 Hz, 2H), 2.68-2.72 (m, 2H), 2.60 (d, 6.8 Hz, 1H), 2.56 (d, 5.6 Hz, 2H), 2.17-2.48 (m, 7H), 2.41 (s, 3H), 2.34 (s, 3H), 1.86 (t, 11.2 Hz, 2H), 1.53-1.79 (m, 17H), 1.35-1.42 (m, 3H), 1.22-1.30 (m, 4H), 0.94-1.05 (m, 1H).

$^{13}$C NMR (100 MHz) δ 173.47, 169.96, 169.36, 169.03, 168.16, 167.00, 145.61, 144.93, 140.64, 138.28, 136.49, 135.14, 131.92, 130.87, 130.66, 129.15, 128.28, 127.37, 126.21, 125.09, 119.13, 117.76, 89.31, 71.45, 71.24, 71.06, 69.56, 69.51, 64.50, 55.78, 53.69, 49.84, 47.43, 46.31, 45.64, 44.71, 43.45, 43.02, 42.82, 41.11, 39.84, 39.08, 38.87, 38.13, 37.51, 33.29, 31.90, 296.11, 28.57, 28.18, 28.06, 25.09, 23.49, 21.97, 21.08, 19.90, 19.67.

HRMS (ESI): Observed 1111.5678 (M+1); 1111.5635, Calculated for C$_{59}$H$_{80}$ClN$_8$O$_{11}$ [M+1]$^+$.

Synthesis of N-(3-(4-(4-carbamoylbenzyl)piperidin-1-yl)propyl)-N-(3-chloro-4-methylphenyl)-1-(21-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-5,17,21-trioxo-3,19-dioxa-6,16-diazahenicosan-1-oyl)piperidine-4-carboxamide, MCC21 (3d)

Yield: 49%, white foam $^1$H NMR (400 MHz, CD$_3$OD) δ 7.77 (d, J=8.4 Hz, 2H), 7.36-7.44 (m, 2H), 7.24 (d, J=7.6 Hz, 2H), 7.15 (d, J=6.8 Hz, 1H), 6.64 (d, J=8.0 Hz, 1H), 6.55 (d, J=8.0 Hz, 1H), 4.48-4.58 (m, 2H), 4.41 (d, J=12.8 Hz, 1H), 4.32 (d, J=14.4 Hz, 1H), 4.26 (d, J=13.2 Hz, 1H), 3.95-4.12 (m, 6H), 3.60-3.72 (m, 3H), 3.12-3.20 (m, 6H), 2.73-2.92 (m, 4H), 2.53-2.63 (m, 3H), 2.40-2.50 (m, 3H), 2.40 (s, 3H), 2.38 (s, 3H), 2.22-2.31 (m, 3H), 1.89-1.97 (m, 2H), 1.42-1.75 (m, 16H), 1.20-1.40 (m, 12H), 0.99-1.12 (m, 2H).

MS (ESI): m/z 1167.6 [M+H]$^+$.

HRMS (ESI): Observed 1167.6296 [M+H]$^+$; 1167.6256, Calculated for C$_{63}$H$_{88}$ClN$_8$O$_{11}$ [M+H]$^+$.

Synthesis of N-(3-(4-(4-carbamoylbenzyl)piperidin-1-yl)propyl)-N-(3-chloro-4-methylphenyl)-1-(22-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-5,18,22-trioxo-3,20-dioxa-6,17-diazadocosan-1-oyl)piperidine-4-carboxamide, MCC22 (3e)

Yield: 65%, white foam $^1$H NMR (400 MHz, CD$_3$OD) δ 7.24 (d, J=8.4 Hz, 2H), 7.77 (d, J=8.4 Hz, 2H), 7.41 (d, J=8.4 Hz, 1H), 7.40 (s, 1H), 7.16 (dd, J=2.0, 8.4 Hz, 1H), 7.16 (dd, J=2.0, 8.4 Hz, 1H), 6.64 (d, J=8.4 Hz, 1H), 6.54 (d, J=8.4 Hz, 1H), 4.50-4.57 (m, 2H), 4.41 (d, J=13.2 Hz, 1H), 4.33 (d, J=14.4 Hz, 1H), 4.24 (d, J=14.4 Hz, 1H), 3.97-4.12 (m, 6H), 3.15-3.72 (m, 3H), 2.75-2.92 (m, 4H), 2.55-2.65 (m, 3H), 2.40-2.50 (m, 3H), 2.45 (d, J=5.6 Hz, 1H), 2.41 (s, 3H), 2.37 (s, 3H), 2.24-2.32 (m, 3H), 1.91 (t, J=11.2 Hz, 2H), 1.40-1.75 (m, 17H), 1.20-1.39 (m, 14H), 1.00-1.12 (m, 1H).

MS (ESI): m/z 1181.6 [M+H]$^+$.

HRMS (ESI): Observed 1181.6431; 1181.6412, Calculated for C$_{64}$H$_{90}$ClN$_8$O$_{11}$ [M+H]$^+$.

Synthesis of N-(3-(4-(4-carbamoylbenzyl)piperidin-1-yl)propyl)-N-(3-chloro-4-methylphenyl)-1-(24-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-5,20,24-trioxo-3,22-dioxa-6,19-diazatetracosan-1-oyl)piperidine-4-carboxamide, MCC24 (3f)

Yield: 87%, pale brown foam $^1$H NMR (400 MHz, CD$_3$OD) δ 7.77 (d, J=8.0 Hz, 2H), 7.38-7.44 (m, 2H), 7.24 (d, J=8.0 Hz, 2H), 7.15 (dd, J=2.0, 7.6 Hz, 1H), 6.64 (d, J=8.0 Hz, 1H), 6.53 (d, J=8.0 Hz, 1H), 4.50-4.60 (m, 2H), 4.41 (d, J=12.8 Hz, 1H), 4.33 (d, J=14.8 Hz, 1H), 4.25 (d, J=14.8 Hz, 1H), 3.98-4.10 (m, 6H), 3.60-3.71 (m, 3H), 3.17-3.28 (m, 4H), 3.12 (t, J=7.2 Hz, 2H), 2.75-2.90 (m, 4H), 2.56-2.62 (m, 3H), 2.42-2.52 (m, 3H), 2.41 (s, 3H), 2.37 (s, 3H), 2.25-2.34 (m, 3H), 1.91 (t, J=12.0 Hz, 2H), 1.40-1.75 (m, 18H), 1.20-1.38 (m, 18H), 1.02-1.13 (m, 1H).

MS (ESI): m/z 1209.8 [M+H]$^+$.

HRMS (ESI): Observed 1209.6737; 1209.6725, Calculated for $C_{66}H_{94}ClN_8O_{11}$ [M+H]$^+$.

Synthesis of Amines (11a-11f)

Synthesis of 11a-11c has been reported previously (Daniels, D. J. Bivalent Ligands as Probes for the Investigation of Opioid Receptor Dimerization. Ph.D. Thesis, University of Minnesota, Minneapolis, Minn. 2006). Using the similar procedures the amines 11d-11f were prepared from their Cbz protected precursors.

Synthesis of N-(9-aminononyl)-2-(2-(((4aS,7S,7aR, 12bS)-4a,9-dihydroxy-3-methyl-2,3,4,4a,5,6,7,7a-octahydro-1H-4,12-methanobenzofuro[3,2-e]isoquinolin-7-yl)amino)-2-oxoethoxy)acetamide (11d)

Yield: 98% brown oil
$^1$H NMR (400 MHz, CD$_3$OD) δ 6.62 (d, J=8.4 Hz, 1H), 6.52 (d, J=8.4 Hz, 1H), 4.48-4.55 (m, 2H), 4.00-4.09 (m, 4H), 3.24 (t, J=7.2 Hz, 2H), 3.15 (t, J=18.4 Hz, 1H), 2.80 (d, J=6.8 Hz, 1H), 2.65 (d, J=7.6 Hz, 2H), 2.58 (dd, J=6.8, 18.4 Hz, 1H), 2.40-2.50 (m, 1H), 2.36 (s, 3H), 2.22-2.32 (m, 2H), 1.65-1.76 (m, 1H), 1.41-1.59 (m, 7H), 1.23-1.40 (m, 10H), 1.00-1.12 (m, 1H).
MS (ESI): Observed m/z 559.4 [M+H]$^+$; 559.3, Calculated for $C_{30}H_{46}N_4O_6$ [M+H]$^+$.

Synthesis of N-(10-aminodecyl)-2-(2-(((4aS,7S,7aR, 12bS)-4a,9-dihydroxy-3-methyl-2,3,4,4a,5,6,7,7a-octahydro-1H-4,12-methanobenzofuro[3,2-e]isoquinolin-7-yl)amino)-2-oxoethoxy)acetamide, (11e)

Yield: ~100% pale yellow oil
$^1$H NMR (400 MHz, CD$_3$OD) δ 6.63 (d, J=8.4 Hz, 1H), 6.52 (d, J=8.4 Hz, 1H), 4.50-4.55 (m, 2H), 4.07 (s, 2H), 4.04 (s, 2H), 3.24 (t, J=7.2 Hz, 1H), 3.16 (d, J=18.8 Hz, 1H), 2.80 (d, J=6.4 Hz, 1H), 2.64 (d, J=7.2 Hz, 1H), 2.58 (dd, J=6.8, 18.8 Hz, 1H), 2.45 (d, J=5.6 Hz, 1H), 2.36 (s, 3H), 2.22-2.34 (m, 2H), 1.64-1.78 (m, 1H), 1.42-1.60 (m, 7H), 1.22-1.38 (m, 12H), 0.98-1.12 (m, 1H).
MS (ESI): Observed m/z 573.5 [M+H]$^+$; 573.4, Calculated for $C_{31}H_{49}N_4O_6$ [M+H]$^+$.

Synthesis of N-(12-aminododecyl)-2-(2-(((4aS,7S, 7aR,12bS)-4a,9-dihydroxy-3-methyl-2,3,4,4a,5,6,7, 7a-octahydro-1H-4,12-methanobenzofuro[3,2-e] isoquinolin-7-yl)amino)-2-oxoethoxy)acetamide, (11f)

Yield: 89% white foam
$^1$H NMR (400 MHz, CDCl$_3$) δ 6.99 (br d, J=8.4 Hz, 1H), 6.68 (d, J=6.8 Hz, 1H), 6.54 (d, J=6.8 Hz, 1H), 4.61 (s, 1H), 4.58 (br s, 1H), 3.92-4.10 (m, 4H), 3.28-3.37 (m, 2H), 3.13 (d, J=18.4 Hz, 1H), 2.68-2.78 (m, 3H), 2.57 (dd, J=6.4, 18.8 Hz, 1H), 2.38-2.45 (m, 1H), 2.35 (s, 3H), 2.20-2.30 (m, 2H), 1.65-1.80 (m, 1H), 1.20-1.60 (m, 23H), 1.05-1.15 (m, 1H).
MS (ESI): Observed m/z 601.6 [M+H]$^+$; 601.4, Calculated for $C_{33}H_{53}N_4O_6$ [M+H]$^+$.

B. Biology

Intracellular Calcium Release.

Briefly, HEK-293 cells were cultured at 37° C. in Dulbelcco's modified Eagle's medium supplemented with 10% fetal bovine serum and 1% Penicillin/Streptomycin. Then 100 mm$^2$ were transiently transfected with CCR$_5$ receptor cDNA using OptiMEM-1 medium (Invitrogen) and Lipofectamine 2000 (Invitrogen, Carlsbad, Calif.) reagent according to manufacturer's protocol (1:2 wt/vol ratio for DNA:Lipofectamine; 16 μg DNA: 32 μl Lipofectamine). The cells were seeded into 96 well plates (half-area; Corning) at 20,000 cells/well after 24 hours and assayed 48 hours after transfection using the FLIPR calcium kit (Molecular Devices) in a Flexstation-III apparatus (Molecular Devices). Cells were incubated with the calcium dye for 45 minutes at 37° C. before the antagonists were added to each well at the concentration listed, and incubated at 37° C. for 15 minutes. The control agonist, CCL$_5$ (RANTES), was added at a concentration that elicited an 80% maximal response in untreated cells (100 nM) to each well and the calcium response measured with and without antagonists for 90 seconds. The change in RFU was calculated by subtracting the minimum relative fluorescent unit (RFU) from the maximum RFU response, replicated 6 times and averaged. Each experiment was repeated at least 3 times and the mean±SEM was plotted for each treatment group. Plates were 80-90% confluent, cells Animals for Antinociceptive Studies for Naivi and LPS-Treatment.

Male ICR-CD1 mice (17-25 g; Harlan, Madison, Wis.), C3H mice (15-20 g, National Cancer Institute, Bethesda, Md.) or TLR4 knock-out mice (gift from Dr. Sabita Roy) were housed, 4 to a small box in a temperature- and humidity-controlled environment with unlimited access to food and water. They were maintained on a 12 h light/dark cycle. All experiments were approved by the Institutional Animal Care and Use Committee of the University of Minnesota (Minneapolis, Minn.).

Antinociceptive Testing.

The tail flick assay is used to test for antinociception described by D'Amour and Smith[64] and modified by Dewey et. al.[65] Mice are held gently in one hand with the tail positioned in the apparatus (Tail Flick Analgesia Meter, Columbus Instruments, Columbus, Ohio) for radiant heat stimulus. The tail-flick response is elicited by applying radiant heat to the dorsal side of the tail. The test latency is measured before drug treatment (control) and again after the drug treatment (test) at the peak time of the compound, a 10 s maximum cut-off time is used to prevent damage to the tail. Antinociception is quantified according to the method of Harris and Pierson[66] as the percent maximal possible effect (% MPE) which is calculated as: % MPE=(Test–Control/ 10–Control)×100

A minimum of three groups of eight to ten mice are used for each dose response curve, and each mouse is used only once. $ED_{50}$ values with 95% confidence intervals (C.I.) are computed with GraphPad Prism 4 by using nonlinear regression methods.

The compounds were tested for acute tolerance by comparing the $ED_{80-90}$ dose measured on day 1 to the same dose administered and retested 24 hours later on the same mouse.

Intrathecal Injections.

Compounds were dissolved in 5% DMSO and diluted to less than 1% DMSO for injection. These compounds were administered in a volume of 5-μl either i.c.v (Haley and McCormick) or intrathecal (i.t.) as described for mice by Hylden and Wilcox[67] in conscious mice. Controls when given either i.c.v. or i.t. with 1% or less DMSO do not show any antinociception. Time course studies, including the times 5, 10, 20, 30 and 60 minutes were used to determine the peak antinociception.

Complete Freund's Adjuvant (CFA)-Mechanical Hyperalgesia.

Before injection of CFA baseline withdrawal thresholds (g) were obtained from a mechanical stimulation using an electronic von Frey anesthesiometer (IITC Life Sciences, Woodland Hills, USA) by applying an accurate force on both left and right hind paw. (2,3) The left hindpaws were then injected (intraplantar) with a 50% solution of CFA (10 µg, Sigma-Aldrich) in water while the mice are under isoflurane anesthesia (10). Twenty-four hours later the withdrawal threshold (g) was again measured prior to and after the test compound i.t. at 10, 20, 30 and 60 minutes to determine the peak time and subsequent $ED_{50}$. % MPE was calculated ((Time-point withdrawal threshold with drug–CFA withdrawal threshold)/(Day 0 withdrawal threshold–CFA withdrawal threshold))*100 (Wade, C. L., et al., *PLoS One* 2013, 8, e79239/1-e79239/11, 11 pp; Martinov, T., et al., *J Vis Exp* 2013, e51212; Sorge, R. E., et al., *J. Neurosci.* 2011, 31, 15450-15454).

Effect of Minocycline in Mice Pretreated by LPS and Blockage of Antinociception of MCC22.

Three separate groups of mice (n=8) were pretreated with 1 mg/kg of LPS (i.p.). At 24 hours the baseline antinociception was measured using the tail flick assay to calculate % MPE. Mice were then injected i.p. with 45 mg/kg of minocycline HCL ((Sigma Aldrich) dissolved in distilled water and gently warmed until clear yellow) at three different time points, one, two and four hours, to confirm that minocycline did not cause antinociception by itself. After each group, mice were injected 1 pmol/mouse MCC22 (i.t.) and 5 minutes later the final antinociception was measured. The dose used for MCC22 is a hundred times the $ED_{50}$ dose of LPS pretreated mice with MCC22. To establish a dose response curve, a separate group of mice were pretreated with LPS for 24 hours—minocycline for 4 hours—1000 pmol/mouse and MCC22 was tested that resulted in 49.35±14.38 the % MPE, and when saline was used instead of MCC22 the % MPE was 6.98±3.55%, Proinflammatory Cytokine, IL-6 ELISA.

Murine primary microglia cell line (BV2) were cultured in DMEM with 10% heat-inactivated fetal bovine serum (FBS), 100 U/ml penicillin, 100 µg/ml streptomycin, 10 µg/ml gentamycin (all from Invitrogen, CA, USA). Cells were harvested on reaching 80% to 90% confluence by treating with 0.25% trypsin containing 1 mM EDTA for 5 minutes at 37° C. Cells (20,000/200 µl) were seeded on flat bottom 96 well plates and treated for 3 hrs with equimolar concentration (200 nM) of MCC22/Minocycline for 3 hrs followed by overnight treatment with LPS (1 µg/ml). At the end of the experiment, IL-6 was estimated by Sandwich ELISA using mouse IL-6 DuoSet kit (R&D Systems, Minneapolis, Minn.) in the culture supernatant.

Molecular Modeling.

All modeling was performed using the Schrodinger modeling package.[68] The approach was adopted from an earlier homology modeling study of GPCR and the design of conjugated bivalent substrate study described in details elsewhere.[69,70] The modeling study of MOR-$CCR_5$ heteromer with its bound MCC22 inhibitor was based on the X-ray crystallographic structures of the beta-FNA-bound MOR (PDB code: 4DKL)[37] and Maraviroc (MRV)-bound $CCR_5$ (PDB code: 4MBS)[38] fusion protein complexes. Structure preparation involved the removal of the non-native T-4 lysozyme subunit from MOR and the rubredoxin subunit from $CCR_5$. The resultant gaps in the intracellular loop 3 (ICL3) of MOR 264-269 and $CCR_5$ 224-227 were homology modeled to generate the contiguous MOR and $CCR_5$ protein model. All missing sidechains and hydrogen atoms were added with standard protein preparation protocols at physiological pH, followed by energy minimization using OPLS-AA 2005 force field[71] with Generalized Born implicit solvent model[72] to optimize all hydrogen-bonding networks.

Due to the technical challenges of docking an extendable bivalent ligand into a heteromer consisting of two distinctive ligand binding sites, the modeling approach was carried out in two stages. First the conjugated heterobivalent MCC22 ligand was divided into its two monovalent pharmacophore units and a linker unit. Each of the pharmacophore units was subsequently docked into its corresponding $CCR_5$ and MOR binding sites using Glide at standard SP protocols. The distance between the two bridging atoms involved in the conjugation of the two pharmacophore units was then determined to provide a reasonable estimate in the optimal length for the linker unit. For MCC22, the two docked pharmacophore units were bridged by a 22 atom spacer linker unit. The final complex model with all the amino residues within 10 Å of bivalent ligand was then refined with restraint energy minimization OPLS2005 force field under implicit Generalized Born solvent model to remove all steric clashes.

Figure 7:
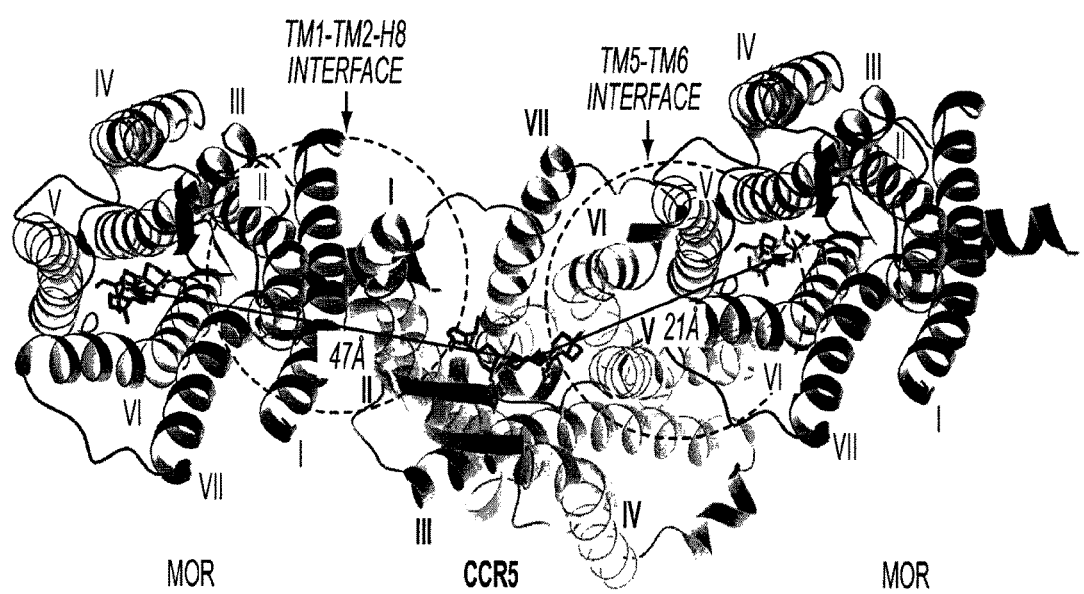
FIG. 7 illustrates a model of TM1-TM2-H8 and TM5-TM6 interfaced $CCR_5$-MOR heteromer.

To determine the potential oligomeric arrangement of the MOR-$CCR_5$ heteromer for MCC22 bivalent ligand binding, superpositioning of the $CCR_5$ docked complex onto the previously observed oligomeric arrangements of MOR with either the TM5-TM6 or the TM1-TM2-H8 interface was carried out (FIG. 7). This approach provided the distal proximity between the two bridging atoms involved in the conjugation of the two docked pharmacophore units and the determination of determination of feasibility for bivalent binding between the two oligomeric arrangements.

Molecular Dynamics Simulation.

To gain better insights into the allosteric effect of MCC22 binding on the structure of MOR-$CCR_5$ heteromer and the specific interactions involved, six 100 ns molecular dynamics (MD) simulation were carried out for the bound and unbound protomers and MOR-$CCR_5$ heteromer. The study is based on an earlier simulation study of the monomeric MOR receptor in an explicit lipid membrane aqueous system.[70] Each of the modeled complex was embedded with a 15 Å buffer region from the edge of the complex within a POPC lipid membrane, and explicit TIP3P[73] water layer at 0.1M NaCl salt concentration as counter ions inside a rectangular box. The long range electrostatic interactions were evaluated by the Particle-Mesh Ewald method under periodic boundary condition with a dielectric constant of 1. Each MD simulation was carried out using DESMOND[74] with default initialization protocol, followed by 100 ns unrestraint production simulation run under constant area isothermal isobaric (NPAT) condition at 300K and 1 atm with OPLS-AA 2005 forcefield. For holo complexes, a force constant of 5 kcal/molÅ restraint was applied to the heavy atoms of the bound ligand during the initialization to ensure proper equilibrium of the protein-ligand interactions prior to the start of the simulation. The stability of the protein was assessed by evaluating the $C_\alpha$RMSD with respect to the minimized starting structure.

Results

Antinociceptive Studies Using Normal and LPS-Pretreated Mice.

Pain is a hallmark of many inflammatory conditions. Intraperitoneal (i.p.) LPS as an inflammation-producing stimulus in mice was used in the present study.[16,34] The target compounds (3a-3d, 4, 5) were administered via intrathecal or intraceboventricular routes to mice that were LPS-pretreated or untreated (control mice). Antinociception was evaluated using the radiant heat-induced tailflick assay.

Morphine was employed as a standard opioid agonist under these conditions. The results are presented in Table 1.

For members 3a-3c of the bivalent MCC series, increasing the number of atoms from 14 to 19 in the spacer that connects the pharmacophores, afforded no change in i.t. antinociception in LPS-pretreated mice. However, on increasing the spacer length to 22 atoms (3c to 3e) a >700-fold potency increase occurred. This is in contrast to the i.t. profile for LPS-untreated control mice where only a potency increase of ~4-fold was observed. The LPS-treated/control potency ratio for 3d (MCC22) is 3070. The i.t. potency ratio, morphine/MCC22 in LPS-pretreated mice was 2400. While morphine and monovalent mu agonist 4 exhibited tolerance upon repeated administration by the i.t. route to LPS-pretreated mice, none was observed for any members (3a-3e) of the MCC series. The structure-activity relationship (SAR) data are consistent with the bridging of protomers in a putative MOR-CCR$_5$ The i.c.v. SAR profile in LPS-pretreated mice for 3a-3e differs significantly from the i.t. data, in that there is no potency increase upon lengthening the spacer from 19 (3c) to 22 (3e) atoms. In this regard, the i.c.v./i.t. potency ratio for MCC22 (3e) is 34,000 suggesting that the putative MOR-CCR$_5$ heteromer resides in the cord but not in the brain. By comparison, the i.c.v./i.t. in control mice was only 11 and reflects profound changes in the putative target heteromer that occur in the inflammatory state.

tor (Takemori, A. E., et al., *Eur. J Pharmacol.* 1981, 70, 445-51). The 96.6 ED$_{50}$ potency ratio (β-FNA-treated/control) supports such involvement.

A comparison of the LPS/tail-flick ED$_{50}$ of MCC22 with that of the CFA-induced mechanical hyperalgesia mouse model revealed overlapping confidence intervals for ED$_{50}$ values between the two assays (Table 2). This suggests that the LPS potency enhancement of MCC22 in mice pretreated with LPS is related primarily to inflammation-induced hyperalgesia.

TABLE 2

Comparison of antinociception in thermal (LPS) and mechanical (CFA) hyperalgesia mouse models

| Compd. (i.t.) | Thermal vs Mechanical Hypersensitivity ED$_{50}$ values (95% CI) pmol/mouse | |
|---|---|---|
| | LPS | CFA |
| Saline | No effect | No effect |
| Morphine | 35 (24-50) | 15 (18-42) |
| MA-19 | 21 (14-34) | 27 (10-22) |
| | No synergy | No synergy |
| MCC14 | 11 (6-9) | 3 (1-7) |
| MCC22 | 0.015 (0.009-0.025) | 0.019 (0.003-0.109) |
| MCC24 | 123 (80-187) | 58 (40-85) |

TABLE 1

Comparison of antinociceptive activity (pmol/mouse) of bivalent ligands that contain MOR agonist/CCR$_5$ antagonist pharmacophores with corresponding monovalent ligands

| Compound | CONTROLS ED$_{50}$ (CI) | | | LPS pretreated (1 mg/kg 24 hours i.p.) ED$_{50}$ (CI) | | |
|---|---|---|---|---|---|---|
| | i.t. | i.c.v. | i.c.v./i.t. ratio | i.t. | i.c.v. | i.c.v./i.t. ratio |
| Morphine | 27.0 (21.2-35.6) | 301 (224-406) | 11.1 | 35.0 (24.3-50.4) | 301 (224-406) | 8.60 |
| 2 TAK-220 | 1000$^a$ 34.2 ± 10.8% | 1000$^a$ 26.2 ± 5.9% | 1 | 740 (429-1278) | 1000$^a$ 7.6 ± 1.5% | —$^e$ |
| 3a (MCC14) | 32.3 (27.3-38.4)$^b$ | 107 (78.2-145)$^c$ | 3.29 | 10.6 (6.05-18.58)$^b$ | 56.41 (33.3-95.6)$^c$ | 5.32 |
| 3b (MCC17) | 371 (253-543)$^c$ | 358 (166-72.2)$^c$ | 3.14 | 10.9 (6.05-18.6)$^b$ | 187 (92.7-378)$^c$ | 6.38 |
| 3c (MCC19) | 166 (54.6-507)$^c$ | 250$^a$ 35.9 ± 9.0% | — | 11.4 (7.04-18.5)$^b$ | 692 (433-1108)$^c$ | 60.7 |
| 3d (MCC21) | 15.83$^b$ (6.2-40.4) | 1000$^a$ 54.5 ± 14.5 | 63.98 | 8.43 (3.0-23.8) 24 hours later, there was still 24% MPE | 1000$^a$ 63.1 ± 45.2 | 118.62 |
| 3e (MCC22) | 45.8 (23.1-90.8)$^b$ | 500$^a$ 49.7 ± 14.9% | 10.93$^e$ | 0.0149 (0.009-0.025)$^b$ | 500$^a$ 41.1 ± 12.9% | ~34,000$^d$ |
| 3f (MCC24) | 336.9$^c$ (138.9-818.3) | 1000$^a$ 27.6 ± 9.1 | ~2.97 | 122.70$^c$ (80-187) | 1000$^a$ 55.7 ± 11.2 | 8.15$^d$ |
| 4 (MA-19) | 113 (86.5-148)$^c$ | 108 (83.1-141)$^c$ | 0.95 | 21.3 (13.6-33.8)$^c$ | 169 (124-230)$^c$ | 7.93 |
| 5 (CCN-19) | 500$^a$ 28.1 ± 11.3% | 505 (228-1118) | — | 1000$^a$ 32.4 ± 12.5% | 1000$^a$ 51.9 ± 12.3% | — |

$^a$The highest dose measured for antinociception and the corresponding percent maximal possible effect for that dose. For acute tolerance, antinociception was again measured 24 hours after the initial dose response curve and the ED$_{80}$ was tested for antinociception; if the same,
$^b$no tolerance; if significantly lower,
$^c$tolerance.
$^d$i.c.v./i.t. ratio calculated using the estimated ED$_{50}$ from the single dose when no full DRC could be obtained.
$^e$The doses measured did not produce an ED$_{50}$ so no ratio could be calculated.

Relative to morphine or its monovalent control ligand 4, the potency of MCC22 is ~1500-fold greater. Confirmation for the involvement of a mu opioid receptor in the action of MCC22 was evaluated in inflamed mice pretreated with β-FNA, a selective alkylating agent of the mu opioid recep- In order to further evaluate the contribution of the 22-atom spacer to the potency of MCC22 in inflamed mice, mixtures of two monovalent ligands consisting of mu agonist 4 either with CCR$_5$ antagonist 5 or TAK220 (2) were evaluated in different ratios to permit calculation of the theoretical $ED_{50}$. The combination of 4+5 behaved as a partial agonist (52% MPE at 510 pmol/mouse), perhaps due to steric interaction of each of the spacers attached to the pharamacophores. However, the mixture of 4+2 functioned as a full agonist ($ED_{50}$=52 pmol/mouse). Based on this value, the potency of MCC22 (3e) is 3500 relative to the mixture (Table 3). It is noteworthy that the bivalents with shorted spacers were 5-fold more potent than the mixture.

TABLE 3

Relative potencies of MCC bivalent ligands relative to a mixture of monovalent mu agonist (4) and $CCR_5$ antagonist (2) in LPS-pretreated mice

| Compound | Relative Potency* |
|---|---|
| 3a | 4.9 |
| 3b | 4.8 |
| 3c | 4.6 |
| 3d | 6.2 |
| 3e | ~3500 |
| 3f | 0.4 |
| 4 + 2 | 1 |

*The theoretical $ED_{50}$[35, 36] of the two monovalents (4 + 2) were evaluated using a 1:35 part solution and was calculated to be 380.65 pmol/mouse. The actual $ED_{50}$ was 52 pmol/mouse and that was the value used to measure relative potency. The combination of 4 + 5 (1:50) was a partial agonist: however at a dose of 1020 pmol/mouse the % MPE was 51.52 ± 14.85.

Modeling and Simulation.

Figure 2A:
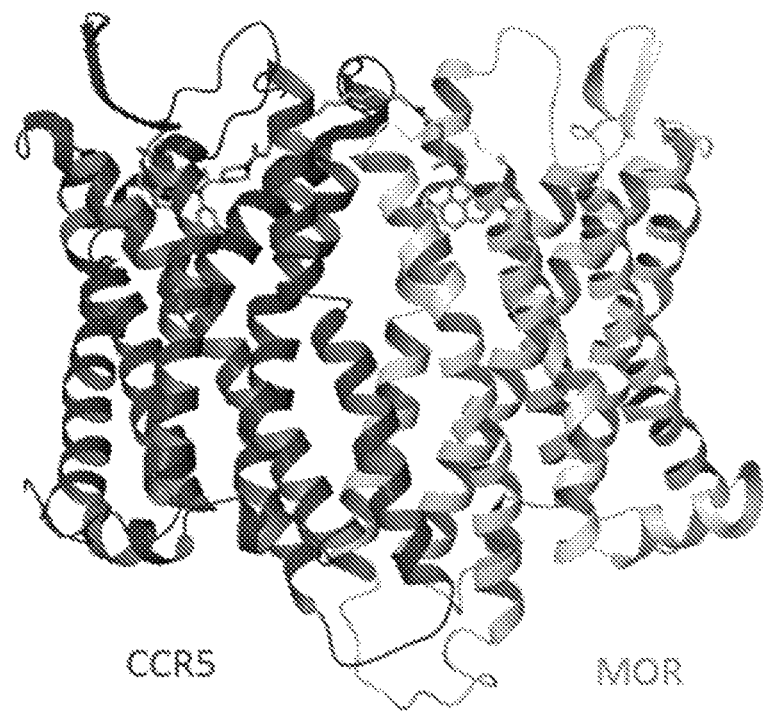
FIG. 2 shows the (A) Side and (B) top view of TM5-TM6 interfaced heteromeric model of MOR-$CCR_5$ complex with MCC22.
Figure 2B:
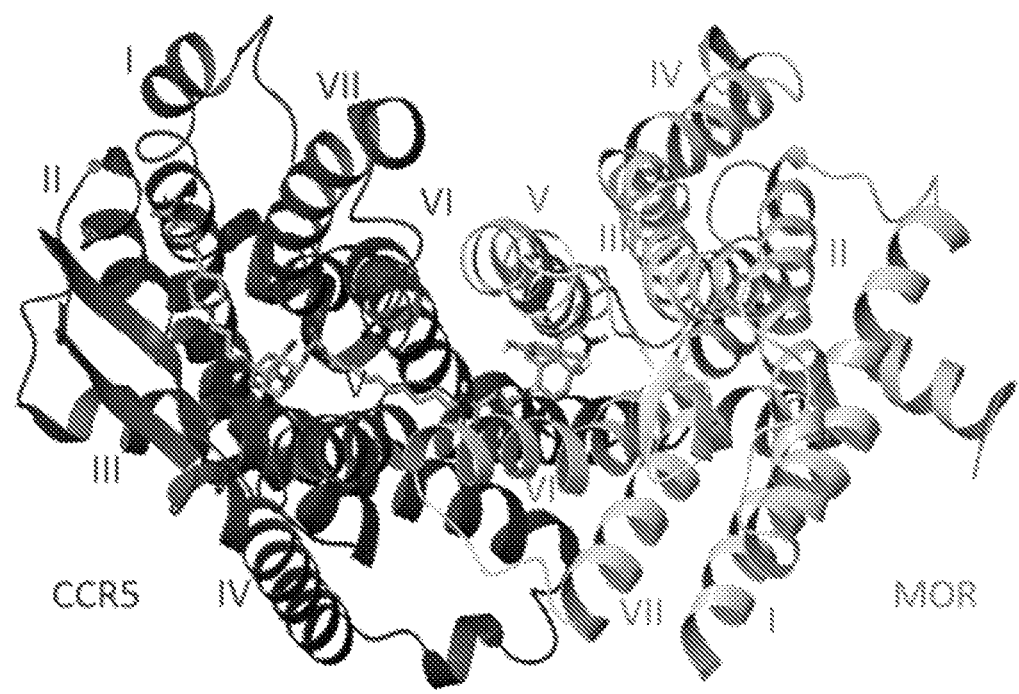
Figure 3A:
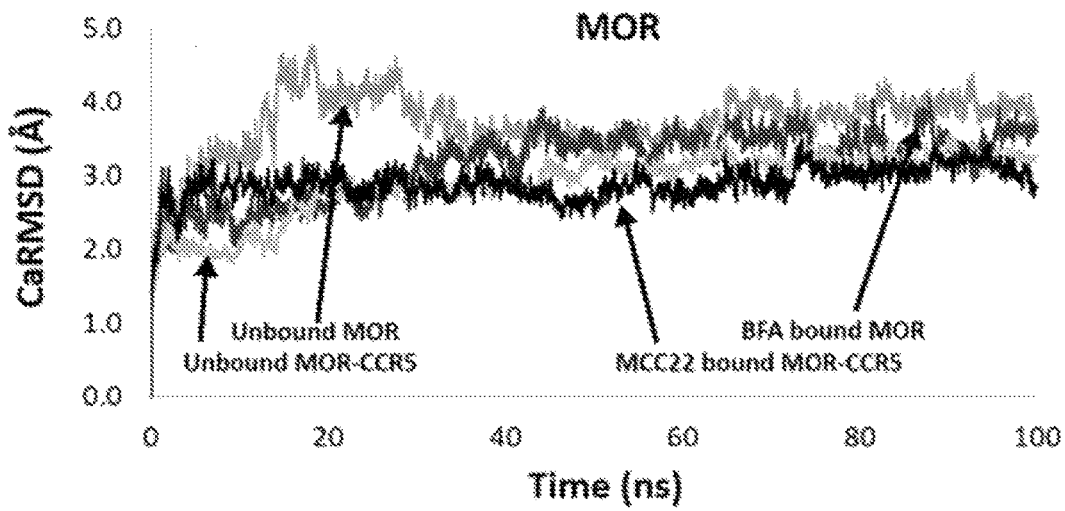
FIGS. 3A and 3B display the CαRMSD of MOR and $CCR_5$ which showed that MCC22 binding reduces the overall conformational flexibility of both MOR and $CCR_5$ in the MOR-$CCR_5$ heteromer.
Figure 3B:
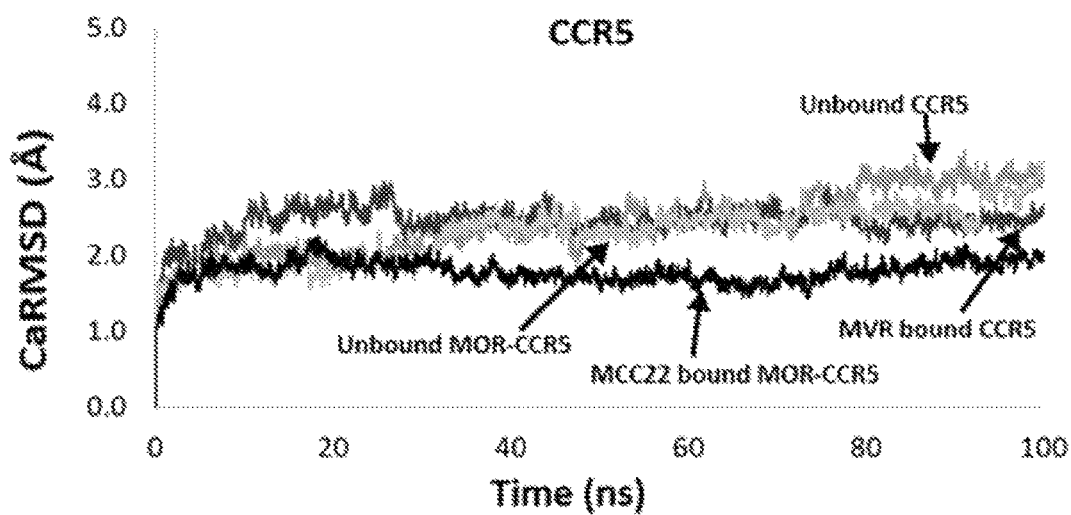
Figure 3C:
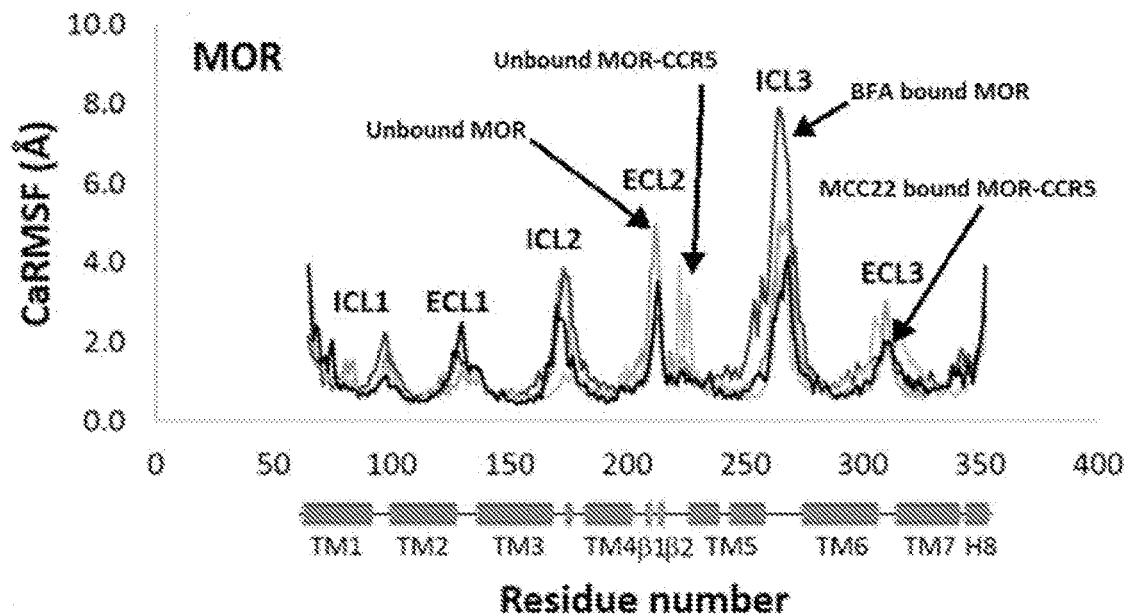
FIGS. 3C and 3D show that significant loss of conformational flexibility was observed in the ICL3 region in MOR between TM5 and TM6 as well as in the ECL3 region of $CCR_5$ between TM6 and TM7 due to MCC22 binding.
Figure 3D:
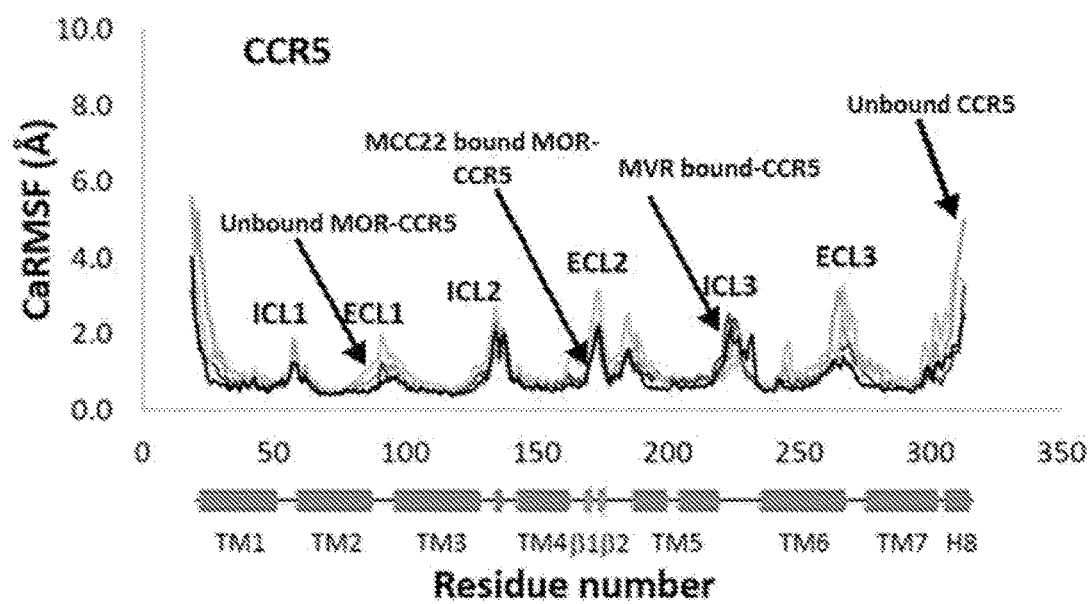

For modeling study of the MOR-$CCR_5$ bivalents, X-ray crystallographic structure of both MOR[37] and $CCR_5$ antagonist Maraviroc bound to $CCR_5$ was utilized.[38] Docking studies revealed that each of the pharmacophores of MCC22 are capable of binding their respective protomers that are interfaced via TM5,6 (FIGS. 2A and 2B). Two critical $CCR_5$ residues were found to be essential for binding,[39,40] namely Glu283 on TM7 which make an electrostatic salt-bridge with central basic nitrogen in the middle of TAK-220, and Ile198 on TM5 which is preserved in a hydrophobic interaction with (3-chloro-4-methylphenyl) groups in TAK-220. The salt bridge interaction of MOR Asp147 with the charged nitrogen atom on morphine was also conserved. Neutralization of these two salt bridges led to subsequent dissociation of MCC22 from the heteromer during MD simulation. MCC22 binding to the heteromer reduces overall conformational flexibility of the heteromer as compared to unbound MOR-$CCR_5$ and its protomeric units (FIGS. 3A and 3B). The major reduction of flexibility was observed in the extracellular loop (ICL3) region of the TM5:TM6 interface of MOR and in the ECL3 region between TM6 and TM7 of $CCR_5$ [FIGS. 3C and 3D].

Effect of MK801 and Minocycline on MCC22 Antinociception on LPS-Pretreated Mice.

As MCC22 possesses exceptional potency under conditions of inflammation, whether or not this effect involves the NMDA receptor was investigated. In this regard, it is well known that LPS activation of TLR4 promotes downstream CNS sensitization in the CNS with hyperalgesia that may arise from activation of the NMDA receptor. In an effort to explore this possibility, LPS-pretreated mice were treated (i.t.) with the NMDA receptor antagonist, MK801, followed by MCC22. This treatment had virtually no effect on MCC22 antinociception. Also, the potency of MCC22 was not reduced in LPS-pretreated TLR4 KO mice. Taken together, these results are consistent with the absence of major involvement of TLR4 or the NMDA receptor in the LPS-induced enhancement of MCC22 antinociception. A possible alternate mechanism by which LPS-induced hyperalgesia promotes inflammatory pain that is inhibited by MCC22 remains to be elucidated.

Figure 4:
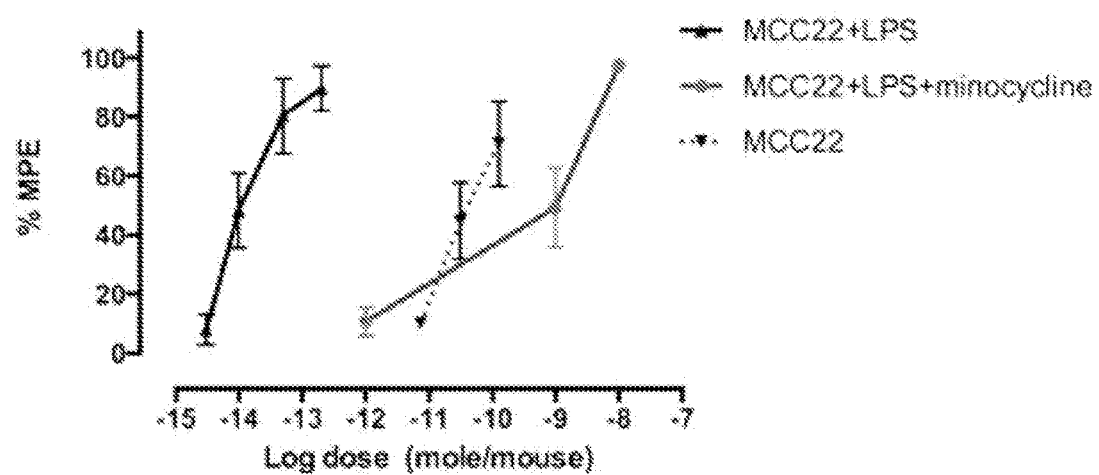
FIG. 4 shows the effect of MCC22 on control or LPS pretreated mice that were injected (45 mg/kg i.p.) with Minocycline prior to testing. LPS/MCC22: 0.015 (0.01-0.03); naïve/MCC22: 45.75 (23.05-90.81); LPS/minocycline/MCC22: 1016 (54-1558).

It has been reported that LPS induces hyperalgesia via activation of spinal microglial cells.[41] In this regard, minocycline is known to suppress hyperalgesia by inhibiting microglial activation. Several research reports suggest that activated glia produce pro-inflammatory chemokines, thereby increasing hyperalgesia that leads to the development and maintenance of inflammatory pain. Since activated glia are known to suppress antinociception produced by opioids,[42,43] the effect of i.p. minocycline[41] on MCC22-induced antinociception in LPS pretreated mice was investigated. Minocycline substantially reduced the antinociceptive effect of MMC22 (FIG. 4). The blockage occurred in time dependent manner as follows (MPE): 60 min (100%); 120 min (52.04%±17.04); 240 min (10.7%±5.17). The blockage therefore suggests that MCC22 reduces LPS-induced hyperalgesia via blockage of the activation of the spinal cord microglia.

MCC22 significantly attenuates generation of proinflammatory cytokine (IL-6) in the presence of LPS.

Figure 8:
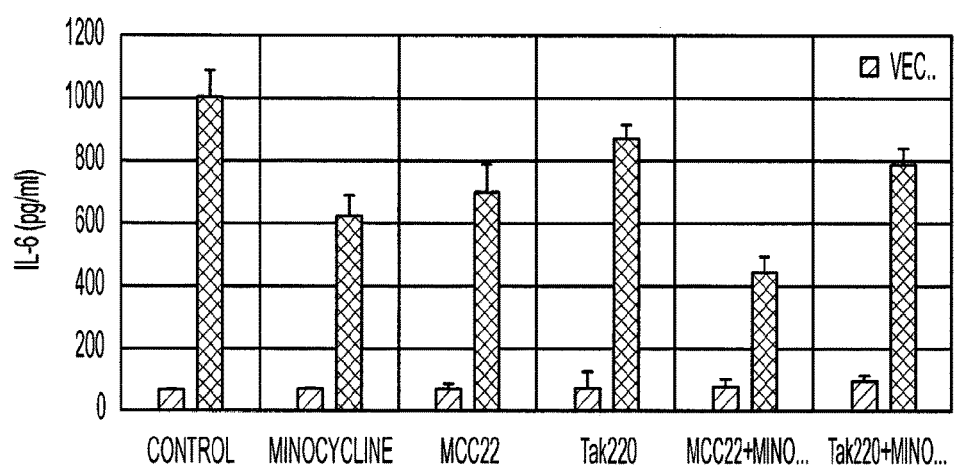
FIG. 8 shows that both MCC22 heterodimer and minocycline suppress the production of proinflammatory cytokine IL-6 generation in the microglia culture supernatant in the presence of LPS stimulant. Cells were pretreated with equimolar concentration (200 nM) of MCC22 and minocycline for 3 hrs followed by overnight treatment with LPS (1 μg/ml). IL-6 sandwich ELISA was performed to detect the level of IL-6 cytokine (pg/ml) in culture supernatant. Data shown are representatives of three separate experiments. Error bars indicate SE derived from triplicate wells. (*P<0.05, **P<0.01, student t-test, two-tailed).
Figure 9:
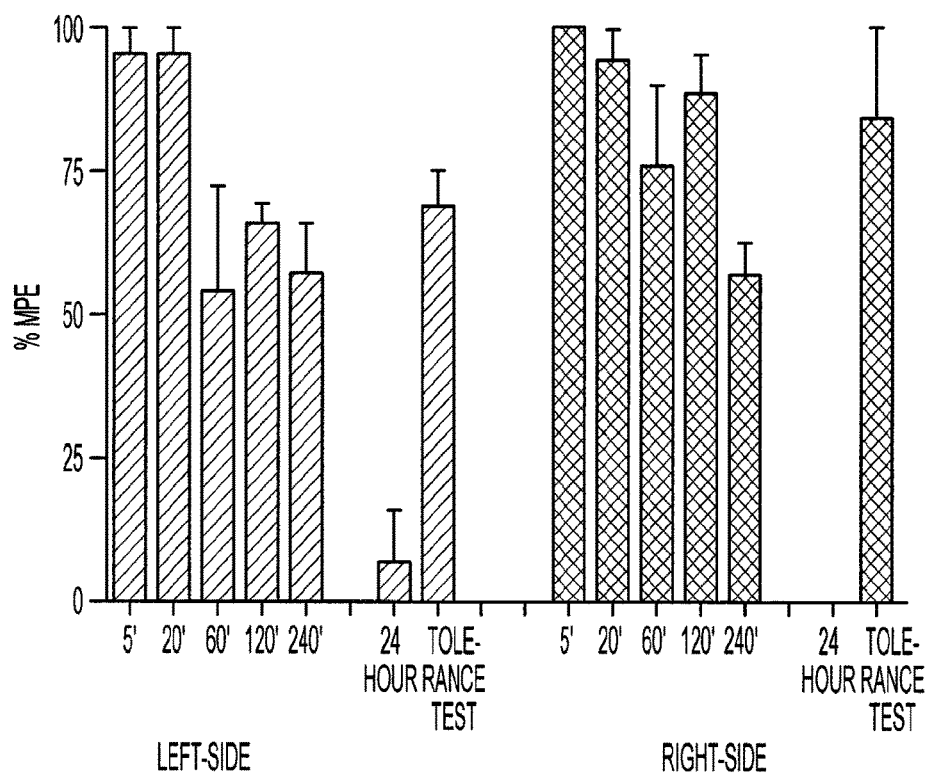
FIG. 9 shows the results of mice treated with MCC22 to block cisplatin-induced neuropathy. Mice (C3H-Jackson) were pretreated 7 days with 1 mg·kg cisplatin (i.p.). MCC22 (10 pmol/mouse) was injected i.t. and measurements were taken at various time points on both the left and right hind paws. After 24 hours, the mice were once again injected with 10 pmol/mouse with MCC22 (i.t.) and the measurement was taken at the 5' peak time.
Figure 10:
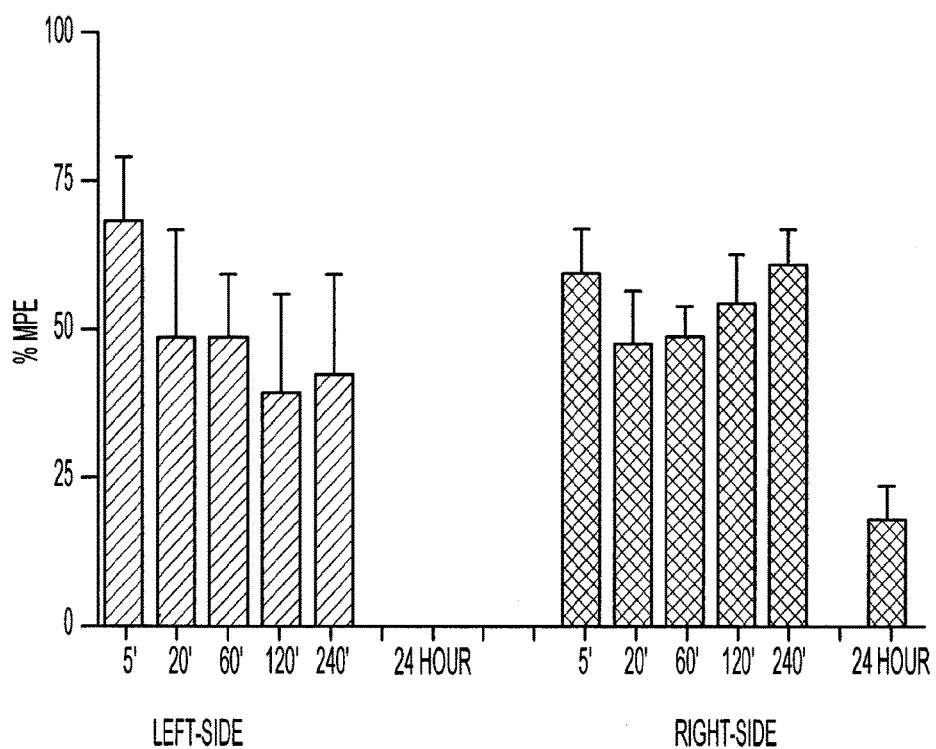
FIG. 10 shows the results of mice treated with MCC22 to block cisplatin-induced neuropathy. Mice (C3H-Jackson) were pretreated 7 days with 1 mg·kg cisplatin (i.p.). MCC22 (0.1 pmol/mouse) was injected i.t. and measurements were taken at various time points on both the left and right hind paws.
Figure 11:
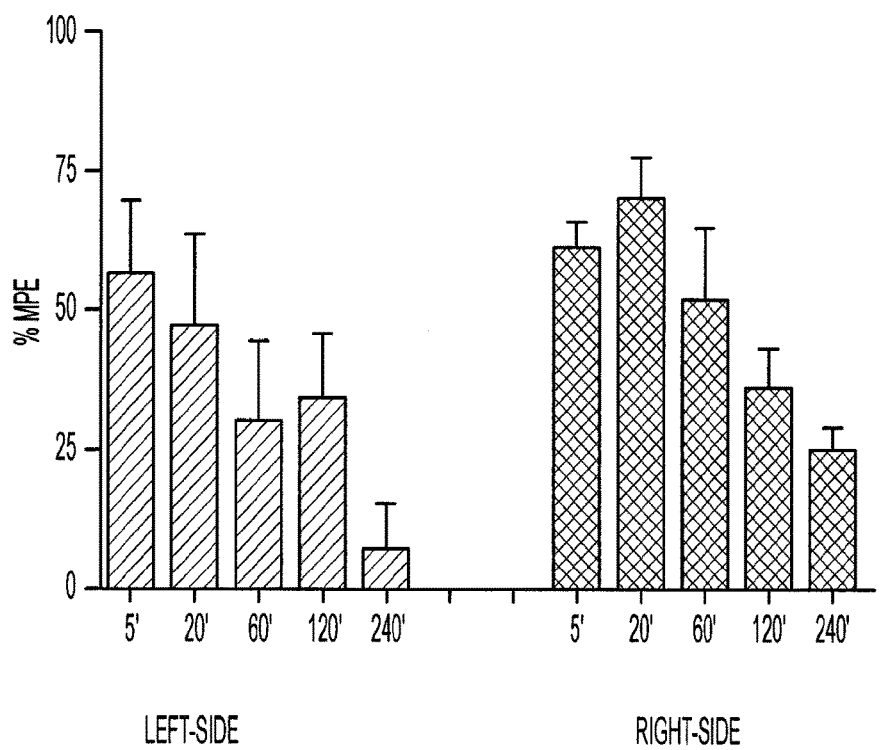
FIG. 11 shows the results of mice treated with MCC22 to block cisplatin-induced neuropathy. Mice (C3H-Jackson) were pretreated 7 days with 1 mg·kg cisplatin (i.p.). MCC22 (0.001 pmol/mouse) was injected i.t. and measurements were taken at various time points on both the left and right hind paws.
Figure 12:
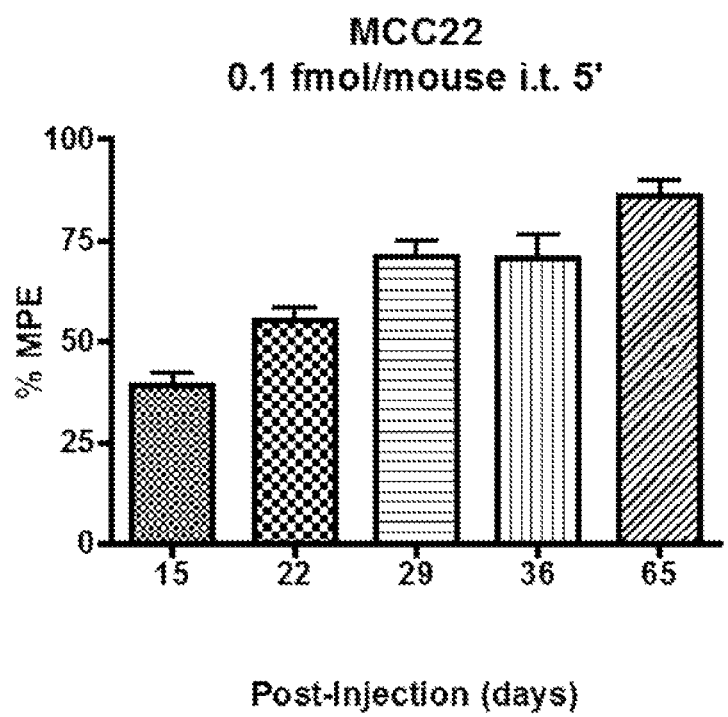
FIG. 12 shows the progressive increase in antinociception produced by intrathecal MCC22 administration as a function of the number of days after cisplatin administration
Figure 14:
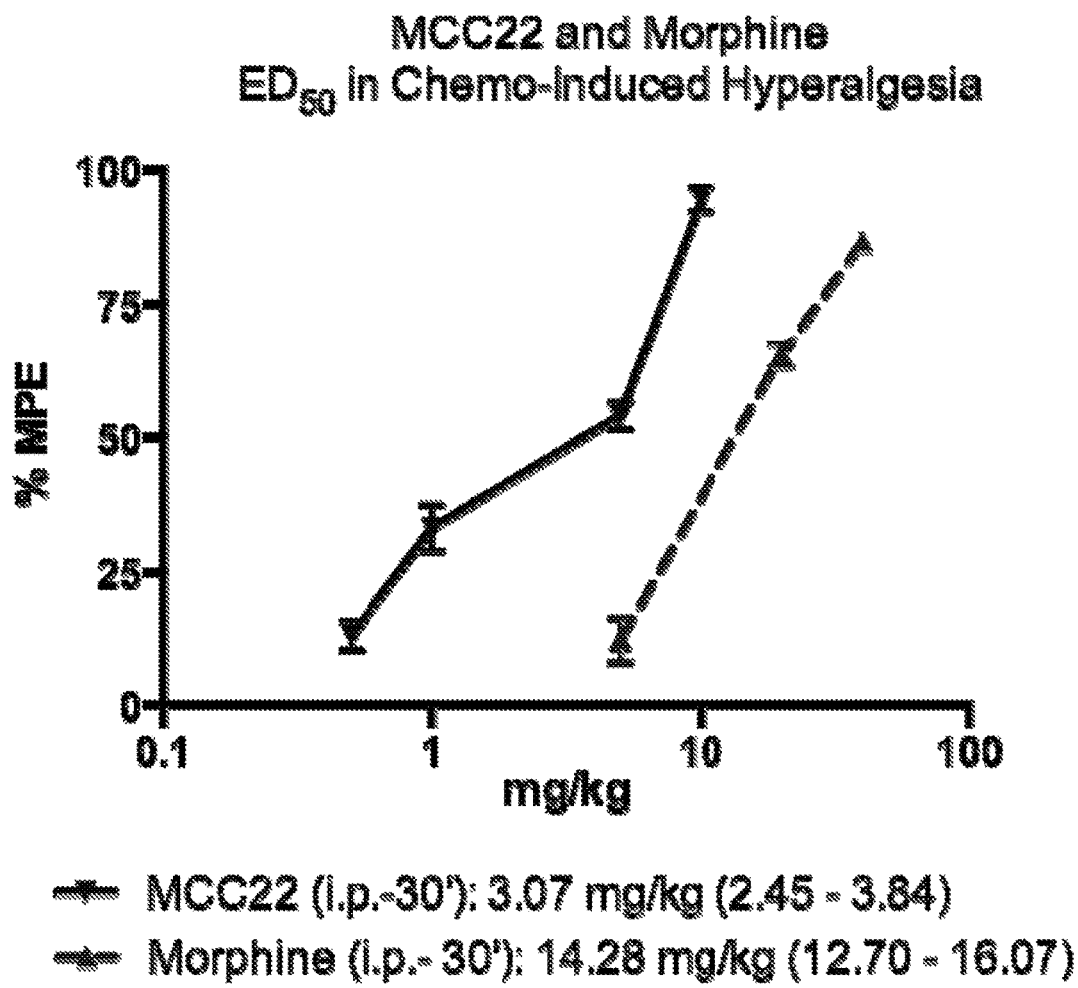
FIG. 14 shows the Comparison of MCC22 and morphine antinociception and their respective potencies shows a significantly lower $ED_{50}$ for MCC22.
Figure 15:
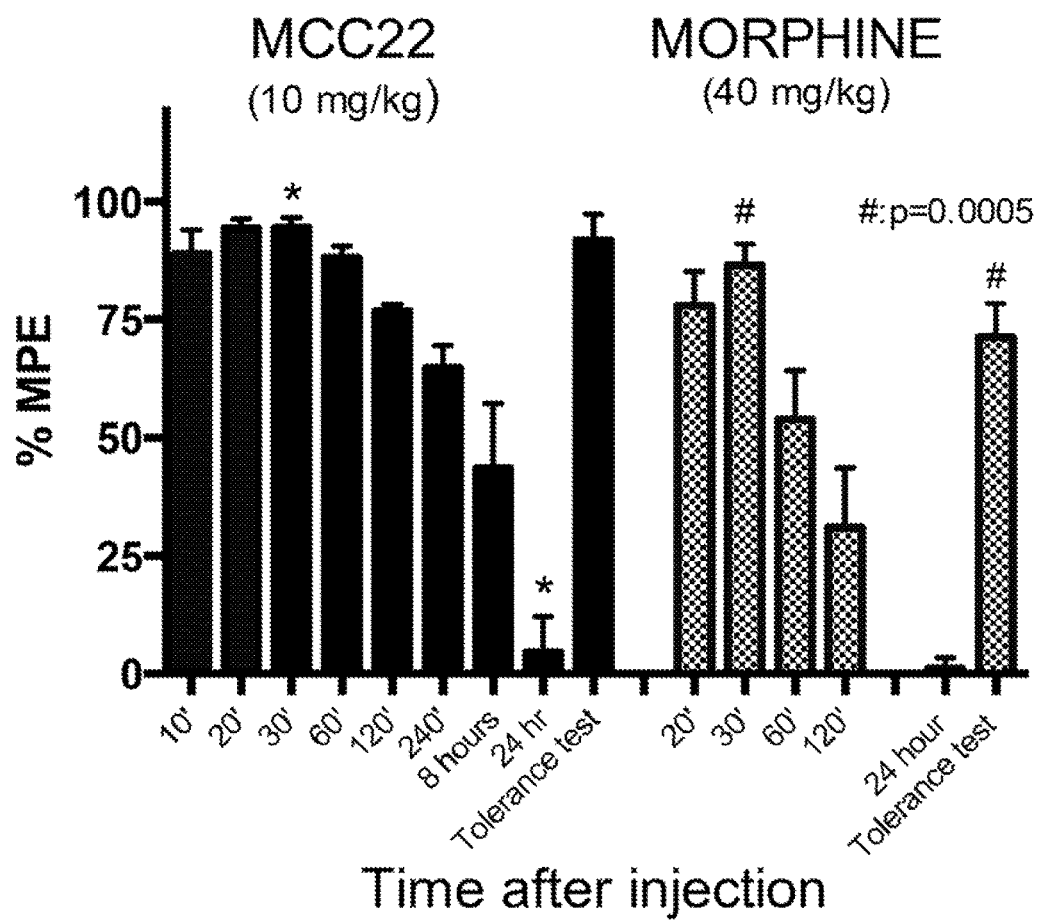
FIG. 15 shows the time-course comparison of i.p. $ED_{80}$ doses of MCC22 and morphine in mice with cisplatin-induced hyperalgesia. Note morphine exhibits 24 h tolerance (p=0.0005).
Figure 16:
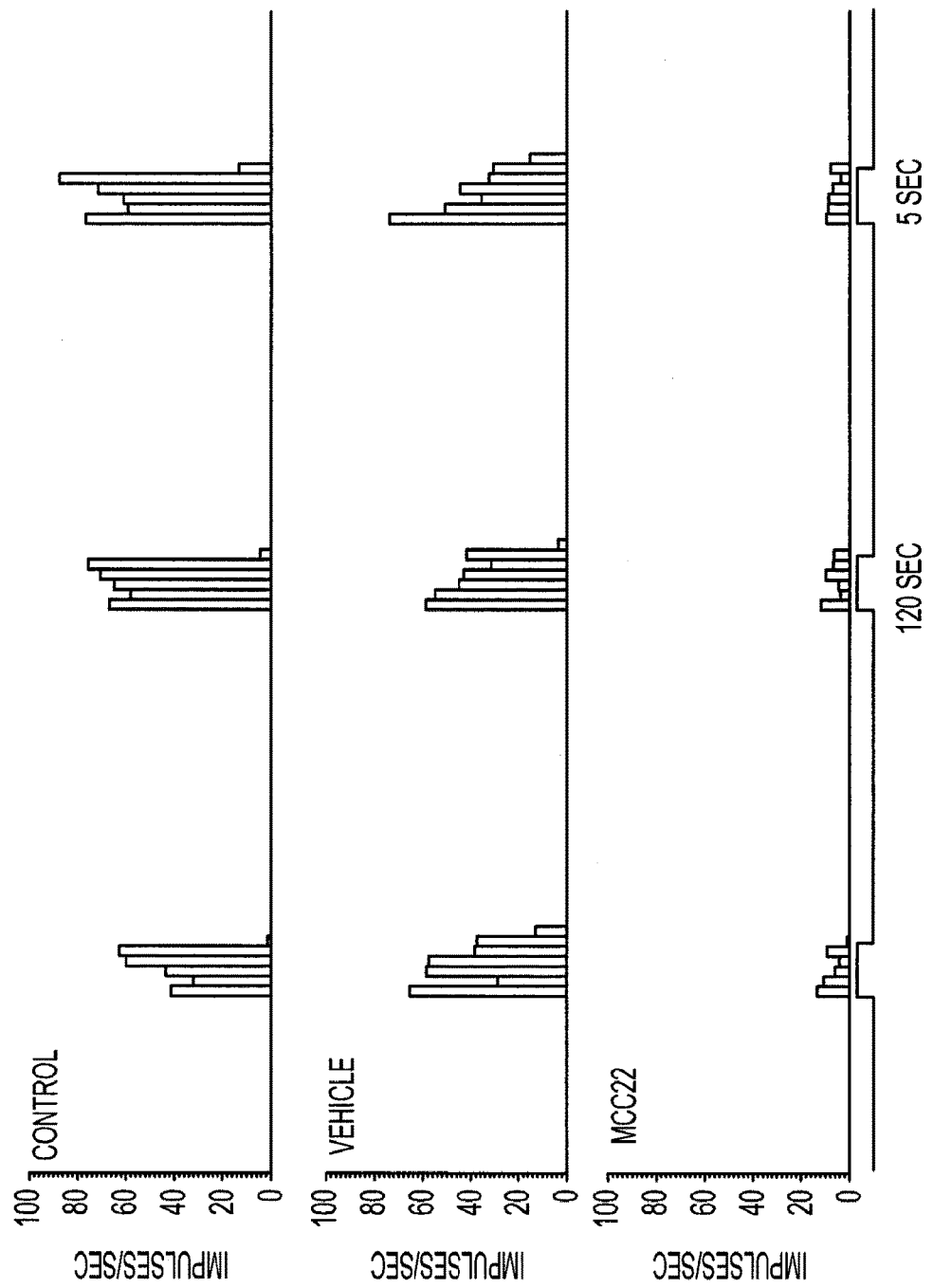
FIG. 16 shows examples of responses evoked by application of a 1.0 g (9.3 mN) von Frey filament to the hind paw (5 sec) within the RF of a WDR neuron following control (Top), vehicle (Middle) and MCC22 (Bottom). The neuron showed significantly reduced responses following administration of the bivalent ligand MCC22. Bin widths 1.0 sec.

Interleukin-6 (IL-6) proinflammatory cytokine plays a significant role in nociception and inflammatory pain.[44] After nerve injury, IL-6 was found to be increased in the corresponding ipsi- and contralateral dorsal and ventral horns, and IL-6 levels paralleled pain behaviors over time[45] Various published articles documented the role of activated spinal microglia in neuropathic pain.[46] In the present study the effect of MCC22 bivalent ligand on LPS-induced proinflammatory cytokine secretion in murine primary microglia was studied. MCC22 significantly attenuated IL-6 secretion in LPS stimulated microglial supernatant ~30% (FIG. 8). Similar results were observed in the presence of minocycline. When combined with minocycline, MCC22, IL-6 secretion was further attenuated, suggesting both minocycline and MCC22 modulate synergistically proinflammatory cytokines in the presence of LPS.

Discussion

The presence of MOR-$CCR_5$ heteromer on membranes of human or monkey lymphocytes and Chinese hamster ovary (CHO) cells coexpressing MOR and $CCR_5$[47] suggest the possibility that such a heteromer may exist in vivo, particularly under inflammatory conditions. Moreover, as $CCR_5$ antagonists are known to inhibit activation of spinal glia in a mouse model and in vitro,[48,49] such heteromers may be relevant to the lower efficacy of morphine under inflammatory conditions that lead to chemokine release. Thus, ligands that activate MOR with concomitant antagonism of $CCR_5$ could represent a promising strategy to develop analgesics with enhanced potency and reduced side effects in the pharmacotherapy of inflammatory pain. Targeting a MOR-$CCR_5$ heteromer in this fashion also may be useful for treatment of painful HIV-related neuropathy.[50]

The ligands synthesized in this study contain pharmacophores derived from the mu opioid agonist, oxymorphone 1,[25] and $CCR_5$ antagonist, TAK-220 (2).[26] The design approach involved connecting these pharmacophores through different length spacers (14 to 22 atoms) to afford the MCC series (3a-31) of bivalent ligands. The selection of spacer lengths were based on prior studies that suggested effective bridging of heteromeric GPCR protomers in the range of 18-22 atoms,[11,27,30-33] and our desire to compare potency changes as a function of spacer length.

Members of the MCC series were administered by intrathecal (i.t.) or intracerebroventricular (i.c.v.) routes to both normal and LPS pretreated mice. LPS was employed because this model is well established for inflammatory pain.[51] Ligands 3a-3c with spacers in the 14-19 atom range afforded $ED_{50}$ values for antinociception in the ~11 pmol range when administered i.t. to LPS pretreated mice. However, the 22-atom spacer homologue, MCC22 (3e), produced antinociception that was at least 700-fold greater ($ED_{50}$ 0.0146 pmol/mouse) than its lower 19-atom spacer homologue MCC19 (3c) and without signs of tolerance (Table 1). The 22-atom spacer length may be well suited to optimally bridge MOR and $CCR_5$ protomers in a putative heteromer. That i.t. MCC22 in LPS pretreated mice produced antinociception that was 34,223-fold greater than by the i.c.v route suggests the MOR-$CCR_5$ heteromer as the putative target in the spinal cord but not the brain.

Molecular modeling studies are entirely consistent with the bridging of MCC22 with a MOR-$CCR_5$ heteromer that possesses a TM5,6 interface (FIGS. 2A and 2B). This interface was observed for a dimer in the crystal structure of MOR.[37] An alternative TM1-TM2-H8 interfaced dimer observed in the crystallographic study possesses a 45 Å distance between binding sites and is therefore not considered as a putative target, given the distal constraint of the linker group at 22 Å (FIG. 7). The modeling also reveals that the shorter spacer homologues 3a-3c in the MCC series are incapable of effective bridging of both pharmacophores of the protomer recognition sites the heteromer.

Since modeling studies indicate that MCC22 binding to the heteromer reduces the overall conformational flexibility of MOR-$CCR_5$ heteromer, its exceptional potency suggests that induction of the unique conformational changes in binding to the heteromer cannot be mimicked by a combination of monovalent ligands. The major reduction of conformational flexibility in MOR-$CCR_5$ that occurs near the TM5-TM6 association interface is consistent with the expected mode of binding of MCC22 and with the finding that it has ~3500-fold greater potency than a mixture of monovalent ligands (4+2) in LPS-pretreated mice.

In contrast to the exceptional i.t. potency of MCC22 in LPS pretreated mice, untreated control mice exhibited an i.t. $ED_{50}$ that was 3131-fold greater, illustrating the dramatic effect of inflammation in enhancing antinociception of MCC22 (Table 1). The magnitude of this effect may in part be due to the LPS-induced upregulation of MOR-$CCR_5$ heteromer. Thus, in the LPS-pretreated mouse model for inflammation, greatly increased spinal expression of cell-surface neuronal or glial MOR and $CCR_5$ may also lead to elevated levels of MOR-$CCR_5$ heteromer[52-57] that could contribute to enhanced potency of MCC22.

It is now established that neuroimmune perturbations arising from spinal cord injury, various medications that include chemotherapy, and a number of diseases, can lead to chronic inflammatory pain mediated via microglia. In view of the efficacy of MCC22 in alleviating inflammatory pain, additional studies with minocycline[58] were conducted as it is a well-established that it selectively inhibits the activation of microglia, thereby reducing the production of inflammatory mediators. Significantly, in inflamed mice pretreated i.p with minocycline, the potent antinociception of i.t. MCC22 in inflamed mice was greatly reduced. As minocycline has been reported to mediate reduction of $CCR_5$[58] as well as $CXCR_4$[59] in HIV-1 infection, it is possible that the effect of MCC22 mediated via inflamed microglia offers the opportunity to explore applications for treatment of chronic inflammatory pain and perhaps neuroAIDS.

In vitro MCC22 effectively attenuated LPS-mediated IL-6 secretion from activated murine microglia significantly. The MCC22-mediated suppression of IL-6 secretion is even more pronounced in the presence of minocycline which is well known to inhibit microglial activation.[60] The cytokine IL-6 signal through the gp130/Jak/STAT pathway[61] plays a key role in the development of neuroinflammation in the spinal cord contributing to pathological pain development. Taken together, MCC22 has potential to be agent for the treatment of neuropathic pain arising from a variety of conditions that promote hyperalgesia.

Example 2

MCC22 attenuates nociception in a murine model of chemotherapy-induced peripheral neuropathy.

Although powerful, pharmacological antineoplastic therapies has led to increased survival for millions of cancer patients, chemotherapeutic agents such as cisplatin produce a number of serious side effects, including peripheral neuropathy (Khasabova I. A., et al., 2012, *J Neurosci.*, 32:7091-101.). Chemotherapy-induced peripheral neuropathy (CIPN) causes sensory disturbances in the extremities including numbness, paresthesia, and pain (Uhelski M. L., et al., 2015, *J Neurophysiol.* 113:1501-1510), and is the primary dose-limiting side effect that reduces efficacy of treatment and ultimately affects survival.

Analgesics typically used to treat neuropathic pain appear to be relatively ineffective in alleviating pain from CIPN as well as display their own display dose-limiting adverse effects, such as those associated with opiates (Cherny N. I., et al. 1994, *Neurology.* 44:857-861). Given the requisite need for superior pharmacological agents in its treatment, the antihyperalgesic effects of a novel bivalent ligand, MCC22, in a murine model of cisplatin chemotherapy-induced neuropathic pain was investigated. MCC22 contains both mu agonist and $CCR_5$ antagonist pharmacophores linked through a 22 atom spacer. Given the existence of opioid receptor heteromers in cultured cells and possibly in vivo (Akgun E., et al., 2015, *J Med Chem.* 58, 8647-8657), MCC22 may be a potent alternative for the treatment of neuropathic pain without attendant side effects.

Methods

Adult male C3H/HeJ mice were tested for mechanical paw withdrawal responses on 2 consecutive days prior to treatment by determining the frequency of hind paw withdrawal evoked by a standard von Frey monofilament with a bending force of 3.9 mN applied to the plantar surface of the hind paws. Mice were then given 1 mg/kg of cisplatin intraperitoneal (i.p.) daily for 7 consecutive days and on day 14 post-injection, mechanical hyperalgesia was assessed. Compounds were administered intrathecally (i.t.) and i.p. weekly to determine peak time effects and ED50/80.

Mice were anesthetized with isoflurane while maintaining core temperature at 37° C. A laminectomy exposed the lumbar spinal cord then mice were secured in a spinal frame. Extracellular recordings from dorsal horn neurons with receptive fields located on the plantar surface of the hind paw were obtained using glass microelectrodes lowered into the spinal cord.

Receptive fields (RFs) of dorsal horn neurons were identified by stroking the skin and applying mild pressure. Neurons were classified functionally as low threshold (LT), wide dynamic range (WDR) and high threshold (HT) using mechanical stimulation of graded intensities. RF areas were mapped using von Frey filaments. The discharge rate of spontaneous activity was recorded for 3 minutes. Mechanical response thresholds were determined and an increasing series of von Frey filaments were applied, each for 5 sec. Action potentials and the time of stimulus application were stored on a computer. Comparisons of discharge rates were made between vehicle and MCC22.

Discussion

Compared to the anti-hyperalgesic effectiveness of the standard opioid agonist morphine, the effects of MCC22 both i.t. (not shown) and i.p. were investigated and it was found that MCC22 given i.t. (ED50: 0.0004 pmol/mouse (0.0002-0.0009 95% CI) was significantly more potent than i.t. morphine (ED50: 27.44 pmol/mouse (16.57-45.43 95% CI) with a peak time of 20 minutes. MCC22 exhibited no tolerance and increased in potency over 115 days. It was also found to be significantly more potent when given i.p. (ED50: 3.07 pmol/mouse (2.45-3.84 95% CI) compared to morphine (ED50: 14.28 pmol/mouse (12.70-16.07 95% CI) with a peak time of 30 minutes and again did not exhibit tolerance. Morphine both i.t. and i.p. showed significant tolerance.

MCC22 potently attenuates hyperalgesia in a cisplatin model of neuropathy and may offer a viable treatment for patients who suffer from CIPN pain without concomitant side effects. Identifying the molecular mechanisms underlying sensitization of dorsal horn neurons may identify novel targets for treating pain associated with chemotherapy-induced neuropathy.

Example 3

MCC22 attenuates nociception in a murine model of sickle cell disease.

Sickle cell disease (SCD) is one of the world's most common inherited diseases, due to a point mutation in hemoglobin that leads to the polymerization of hemoglobin S, giving red blood cells (RBCs) their sickle shape. The hallmarks of SCD are hemolysis and vaso-occlusion. Vaso-occlusive crises (VOC) frequently occur in response to inflammatory and hypoxic conditions such as infections, surgery, etc. Pain is a major defining characteristic of SCD starting early in life and continuing throughout adulthood. VOC-induced pain can be chronic or episodic and unpredictable, requiring frequent hospitalizations and analgesics. Opioids, predominantly morphine, have been the mainstay treatment for pain management of SCD but pose a serious challenge attributed to the many adverse side effects, including tolerance, respiratory depression, sedation, nausea, constipation, pruritus, and dependence. Given that analgesics characteristically used to treat pain appear to be relatively ineffective in alleviating pain associated with SCD as well as display their own dose-limiting adverse effects, there exists a requisite need for superior pharmacological agents in its treatment. The bivalent ligand MCC22, is highly effective as an analgesic in a murine model of SCD. MCC22 (MW=1255) contains both mu agonist and chemokine CCR5 antagonist pharmacophores that are linked through a 22-atom-spacer. It was designed specifically to target the mu opiate receptor (MOR)-CCR5 heteromer, as there is evidence for crosstalk between MOR and CCR5 in cultured cells that reduces the efficacy of opioid analgesics employed in SCD. Intrathecal (i.t.) MCC22 was potent in reducing the mechanical and heat hyperalgesia in Complete Freund's Adjuvant (CFA) and lipopolysaccharide (LPS) inflammatory pain assays. $ED_{50}$s for the i.t. administration were 0.019 and 0.015 pmol/mouse, respectively. MCC22 when given intraperitoneally (i.p.) to LPS pretreated mice had an $ED_{50}$ of 5.6 µmol/kg. The effect of MCC22 in alleviating pain in SCD mice was also investigated.

Methods

Townes transgenic humanized mice expressing sickle hemoglobin (HbSS/HbAS) and normal human hemoglobin (HbAA) controls (4-12 weeks of age, 20-25 g) were used in this study. Mice were characterized for hyperalgesia by quantifying cutaneous mechanical sensitivity of the hind paw and forelimb grip force. Mechanical sensitivity of the hind paw was evaluated by determining the frequency of withdrawal responses and paw withdrawal threshold. The frequency of paw withdrawal evoked by a standard von Frey monofilament with a bending force of 9.3 mN applied to the plantar surface of the hind paws was determined from 10 trials on each paw. Withdrawal threshold was determined using an electronic von Frey anesthesiometer pressed against the plantar surface with increasing force until withdrawal occurred. To assess deep tissue hyperalgesia, the tensile force of peak forelimb exertion was measured using a computerized grip force meter. To evaluate the analgesic effects of MCC22, paw withdrawal frequency was determined before and at various times after administration of 8.0 mol/kg i.p.

Discussion

Figure 17A:
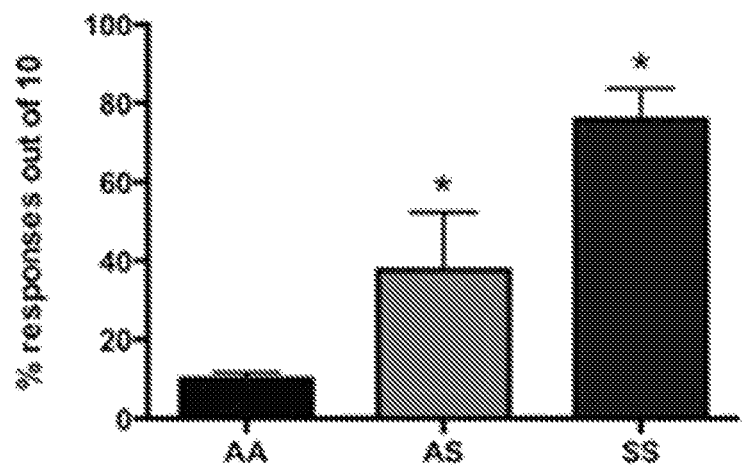
FIGS. 17A, 17B, 17C and 17D show testing results of Hbss sickle mice and HbAS and HbAA controls in 17A paw withdrawal frequency, 17B mechanical threshold, 17C grip force and 17D hyperalgesia after administration of MCC22.
Figure 17B:
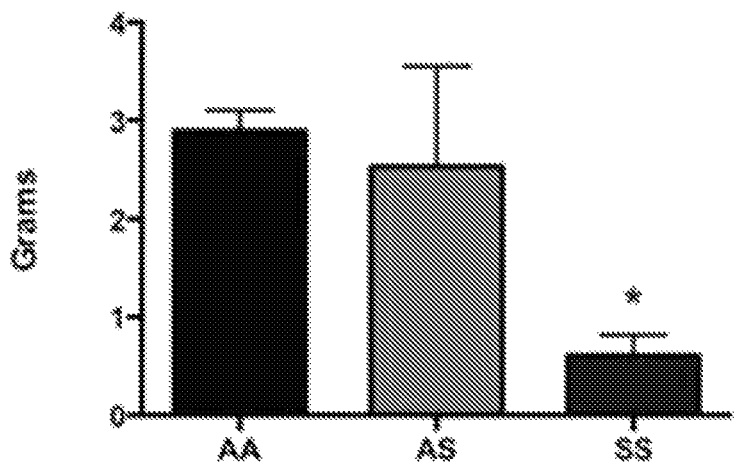
Figure 17C:
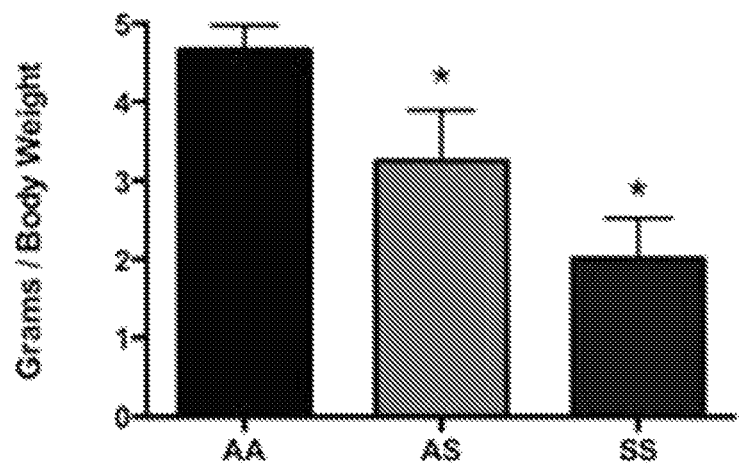
Figure 17D:
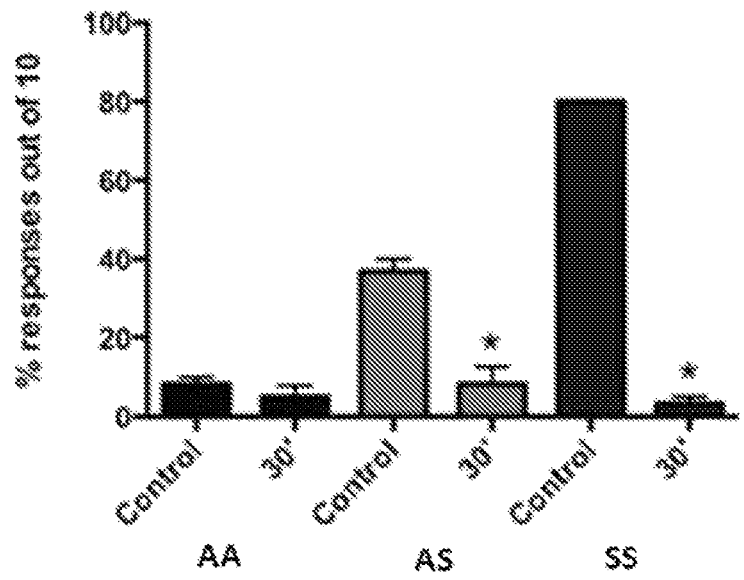

Pain Characterization: HbSS sickle mice exhibited robust mechanical hyperalgesia as shown by a significant increase in paw withdrawal frequency compared to HbAS and HbAA controls (FIG. 17A, p<0.001). Paw withdrawal frequency in HbAS mice was also greater than those for HbAA mice (p<0.001), but less than HbSS mice. HbSS mice had lower mechanical withdrawal thresholds compared to both HbAS and HbAA mice (FIG. 17B, p<0.001), while HbAS did not differ from HbAA mice. HbSS and HbAS mice also displayed lower forelimb grip force compared to HbAA mice (FIG. 17C, p<0.001), although grip force in HbSS was lower than HbAS mice (p<0.001). Administration of MCC22 (8.0 µmol/kg i.p.) reduced hyperalgesia within 30 minutes as evidenced by a decrease in paw withdrawal frequency in both HbSS and HbAS mice (FIG. 17D, p<0.001).

Hyperalgesia was demonstrated in both HbAS and HbSS mice. MCC22 potently attenuated mechanical hyperalgesia in these SCD mice. The use of bivalent ligands that target heteromers involved in signaling pain may offer novel and effective treatments for pain in patients with SCD. Thus, an analgesic with potential anti-inflammatory and mu-agonist activity may provide a novel approach to sickle pain.

1. Muralidharan, A. & Smith, M. T. Pathobiology and management of prostate cancer-induced bone pain: recent insights and future treatments. *Inflammopharmacology* 21, 339-363 (2013).
2. Gutstein, H. B. & Akil, H. in Goodman and Gillman's The pharmacological Basis of Therapeutics—11$^{th}$ Ed. Chapter 21 opioid analgesics. The McGraw-Hill Companies, Inc., USA (2006).
3. Fujita, W., Gomes, I. & Devi, L. A. Revolution in GPCR signalling: opioid receptor heteromers as novel therapeutic targets: IUPHAR Review 10. *Br. J. Pharmacol.* 171, 4155-4176 (2014).
4. Abdelhamid, E. E., Sultana, M., Portoghese, P. S. & Takemori, A. E. Selective blockage of delta opioid receptors prevents the development of morphine tolerance and dependence in mice. *J. Pharmacol. Exp. Ther.* 258, 299-303 (1991).

5. Kest, B., Lee, C. E., McLemore, G. L. & Inturrisi, C. E. An antisense oligodeoxynucleotide to the delta opioid receptor (DOR-1) inhibits morphine tolerance and acute dependence in mice. *Brain Res. Bull.* 39, 185-188 (1996).
6. Zhu, Y. et al. Retention of supraspinal delta-like analgesia and loss of morphine tolerance in δ opioid receptor knockout mice. *Neuron* 24, 243-252 (1999).
7. Ong, E. W. & Cahill, C. M. Molecular perspectives for mu/delta opioid receptor heteromers as distinct, functional receptors. *Cells* 3, 152-179, 128 pp. (2014).
8. Yekkirala, A. S. et al. Clinically Employed Opioid Analgesics Produce Antinociception Opioid Receptor Heteromers in Rhesus Monkeys. *ACS Chem. Neurosci.* 3, 720-727 (2012).
9. Gupta, A., Decaillot, F. M. & Devi, L. A. Targeting opioid receptor heterodimers: strategies for screening and drug development. *AAPS J.* 8, E153-E159 (2006).
10. Milligan, G. G-protein-coupled receptor heterodimers: pharmacology, function and relevance to drug discovery. *Drug Discovery Today* 11, 541-549 (2006).
11. Daniels, D. J. et al. Opioid-induced tolerance and dependence in mice is modulated by the distance between pharmacophores in a bivalent ligand series. *Proc. Natl. Acad. Sci. U.S.A.* 102, 19208-19213 (2005).
12. Yekkirala, A. S., Kalyuzhny, A. E. & Portoghese, P. S. An Immunocytochemical-Derived Correlate for Evaluating the Bridging of Heteromeric Mu-Delta Opioid Protomers by Bivalent Ligands. *ACS Chem. Biol.* 8, 1412-1416 (2013).
13. Yekkirala, A. S. et al. N-naphthoyl-β-naltrexamine (NNTA), a highly selective and potent activator of μ/κ-opioid heteromers. *Proc. Natl. Acad. Sci. U.S.A.* 108, 5098-5103, S5098/5091-S5098/5095 (2011).
14. Le Naour, M. et al. Putative Kappa Opioid Heteromers As Targets for Developing Analgesics Free of Adverse Effects. *J. Med. Chem.* 57, 6383-6392 (2014).
15. Kenakin, T. & Christopoulos, A. Signalling bias in new drug discovery: detection, quantification and therapeutic impact. *Nat. Rev. Drug Discovery* 12, 205-216 (2013).
16. Akgün, E. et al. Ligands that interact with putative MOR-mGluR5 heteromer in mice with inflammatory pain produce potent antinociception. *Proceedings of the National Academy of Sciences* 110, 11595-11599 (2013).
17. Smeester, B. A., Lunzer, M. M., Akgun, E., Beitz, A. J. & Portoghese, P. S. Targeting putative mu opioid/metabotropic glutamate receptor-5 heteromers produces potent antinociception in a chronic murine bone cancer model. *Eur. J. Pharmacol.* 743, 48-52 (2014).
18. White, F. A., Jung, H. & Miller, R. J. Chemokines and the pathophysiology of neuropathic pain. *Proc. Natl. Acad. Sci. U.S.A.* 104, 20151-20158 (2007).
19. Ramesh, G., MacLean, A. G. & Philipp, M. T. Cytokines and chemokines at the crossroads of neuroinflammation, neurodegeneration, and neuropathic pain. *Mediators Inflammation,* 480739, 480721 pp. (2013).
20. Lee, Y. K. et al. Decreased pain responses of C—C chemokine receptor 5 knockout mice to chemical or inflammatory stimuli. *Neuropharmacology* 67, 57-65 (2013).
21. Rogers, T. J. & Peterson, P. K. Opioid G protein-coupled receptors: signals at the crossroads of inflammation. *Trends Immunol.* 24, 116-121 (2003).
22. Mahajan, S. D. et al. Morphine modulates chemokine gene regulation in normal human astrocytes. *Clin. Immunol.* (San Diego, Calif., U. S.) 115, 323-332 (2005).
23. Happel, C., Steele, A. D., Finley, M. J., Kutzler, M. A. & Rogers, T. J. DAMGO-induced expression of chemokines and chemokine receptors: the role of TGF-β1. *J. Leukocyte Biol.* 83, 956-963 (2008).
24. Alkhatib, G. The biology of CCR5 and CXCR4. *Curr Opin HIV AIDS* 4, 96-103 (2009).
25. Weiss, U. Derivatives of morphine. I. 14-Hydroxydihydromorphinone. *J. Am. Chem. Soc.* 77, 5891-5892 (1955).
26. Takashima, K. et al. Highly potent inhibition of human immunodeficiency virus type 1 replication by TAK-220, an orally bioavailable small-molecule CCR5 antagonist. *Antimicrob. Agents Chemother.* 49, 3474-3482 (2005).
27. Aceto, M. D. et al. MDAN-21: A Bivalent Opioid Ligand Containing mu-Agonist and Delta-Antagonist Pharmacophores and Its Effects in Rhesus Monkeys. *International Journal of Medicinal Chemistry* 2012, 1-6 (2012).
28. Le Naour, M. et al. Bivalent Ligands That Target μ Opioid (MOP) and Cannabinoid1 (CB1) Receptors Are Potent Analgesics Devoid of Tolerance. *J. Med. Chem.* 56, 5505-5513 (2013).
29. Zheng, Y. et al. Induced Association of μ Opioid (MOP) and Type 2 Cholecystokinin (CCK2) Receptors by Novel Bivalent Ligands. *J Med. Chem.* 52, 247-258 (2009).
30. Xie, Z., Bhushan, R. G., Daniels, D. J. & Portoghese, P. S. Interaction of bivalent ligand KDN21 with heterodimeric delta-kappa opioid receptors in human embryonic kidney 293 cells. *Mol. Pharmacol.* 68, 1079-1086 (2005).
31. Bhushan, R. G., Sharma, S. K., Xie, Z., Daniels, D. J. & Portoghese, P. S. A bivalent ligand (KDN-21) reveals spinal delta and kappa opioid receptors are organized as heterodimers that give rise to delta(1) and kappa(2) phenotypes. Selective targeting of delta-kappa heterodimers. *J. Med. Chem.* 47, 2969-2972 (2004).
32. Daniels, D. J., Kulkarni, A., Xie, Z., Bhushan, R. G. & Portoghese, P. S. A bivalent ligand (KDAN-18) containing delta-antagonist and kappa-agonist pharmacophores bridges delta2 and kappa1 opioid receptor phenotypes. *J. Med. Chem.* 48, 1713-1716 (2005).
33. Zhang, S., Yekkirala, A., Tang, Y. & Portoghese, P. S. A bivalent ligand (KMN-21) antagonist for mu/kappa heterodimeric opioid receptors. *Bioorg. Med. Chem. Lett.* 19, 6978-6980 (2009).
34. Calil, I. L. et al. Lipopolysaccharide induces inflammatory hyperalgesia triggering a TLR4/MyD88-dependent cytokine cascade in the mice paw. *PLoS One* 9, e90013/90011-e90013/90018, 90018 pp. (2014).
35. Guo, X.-h., Fairbanks, C. A., Stone, L. S. & Loh, H. H. DPDPE-UK14,304 synergy is retained in mu opioid receptor knockout mice. *Pain* 104, 209-217 (2003).
36. Tang, Y., Yang, J., Lunzer, M. M., Powers, M. D. & Portoghese, P. S. A κ Opioid Pharmacophore Becomes a Spinally Selective κ-δ Agonist When Modified with a Basic Extender Arm. *ACS Med. Chem. Lett.* 2, 7-10 (2011).
37. Manglik, A. et al. Crystal structure of the μ-opioid receptor bound to a morphinan antagonist. *Nature* (London, U K) 485, 321-326 (2012).
38. Tan, Q. et al. Structure of the CCR5 Chemokine Receptor-HIV Entry Inhibitor Maraviroc Complex. *Science* (Washington, D.C., U.S.) 341, 1387-1390 (2013).
39. Kondru, R. et al. Molecular interactions of CCR5 with major classes of small-molecule anti-HIV CCR5 antagonists. *Mol. Pharmacol.* 73, 789-800 (2008).
40. Nishikawa, M. et al. Analysis of binding sites for the new small-molecule CCR5 antagonist TAK-220 on human CCR5. *Antimicrob. Agents Chemother.* 49, 4708-4715 (2005).
41. Yoon, S. Y., Patel, D. & Dougherty, P. M. Minocycline blocks lipopolysaccharide induced hyperalgesia by suppression of microglia but not astrocytes. *Neuroscience (Amsterdam, Neth.)* 221, 214-224 (2012).
42. Watkins, L. R., Hutchinson, M. R., Johnston, I. N. & Maier, S. F. Glia: novel counter-regulators of opioid analgesia. *Trends Neurosci.* 28, 661-669 (2005).
43. Vallejo, R., Tilley, D. M., Vogel, L. & Benyamin, R. The role of glia and the immune system in the development and maintenance of neuropathic pain. *Pain Pract* 10, 167-184 (2010).
44. De Jongh, R. F. et al. The role of interleukin-6 in nociception and pain. *Anesth. Analg.* (Baltimore, Md., U.S.) 96, 1096-1103 (2003).
45. Dubovy, P., Brazda, V., Klusakova, I. & Hradilova-Svzenska, I. Bilateral elevation of interleukin-6 protein and mRNA in both lumbar and cervical dorsal root ganglia following unilateral chronic compression injury of the sciatic nerve. *J Neuroinflammation* 10, 55 (2013).
46. Zai, L. J. & Wrathall, J. R. Cell proliferation and replacement following contusive spinal cord injury. *Glia* 50, 247-257 (2005).
47. Chen, C. et al. Heterodimerization and cross-desensitization between the mu-opioid receptor and the chemokine CCR5 receptor. *Eur. J. Pharmacol.* 483, 175-186 (2004).
48. Padi, S. S. V. et al. Attenuation of rodent neuropathic pain by an orally active peptide, RAP-103, which potently blocks CCR2- and CCR5-mediated monocyte chemotaxis and inflammation. *Pain* 153, 95-106 (2012).
49. Pert, C. & Ruff, M. Modified peptide that reduces pain in peripheral neuropathy. WO2012109464A2 (2012).
50. Smith, H. S. Treatment considerations in painful HIV-related neuropathy. *Pain Physician* 14, E505-524 (2011).
51. Takaki, J. et al. L-glutamate released from activated microglia downregulates astrocytic L-glutamate transporter expression in neuroinflammation: the 'collusion' hypothesis for increased extracellular L-glutamate concentration in neuroinflammation. *J Neuroinflammation* 9, 275 (2012).
52. Mousa, S. A., Machelska, H., Schafer, M. & Stein, C. Immunohistochemical localization of endomorphin-1 and endomorphin-2 in immune cells and spinal cord in a model of inflammatory pain. *J Neuroimmunol.* 126, 5-15 (2002).
53. Morinville, A., Cahill, C. M., Kieffer, B., Collier, B. & Beaudet, A. Mu-opioid receptor knockout prevents changes in delta-opioid receptor trafficking induced by chronic inflammatory pain. *Pain* 109, 266-273 (2004).
54. Ballet, S. et al. Expression and G-protein coupling of mu-opioid receptors in the spinal cord and dorsal root ganglia of polyarthritic rats. *Neuropeptides* 37, 211-219 (2003).
55. Zaringhalam, J., Manaheji, H., Mghsoodi, N., Farokhi, B. & Mirzaiee, V. Spinal µ-opioid receptor expression and hyperalgesia with dexamethasone in chronic adjuvant-induced arthritis in rats. *Clin. Exp. Pharmacol. Physiol.* 35, 1309-1315 (2008).
56. Puehler, W. et al. Rapid upregulation of µ opioid receptor mRNA in dorsal root ganglia in response to peripheral inflammation depends on neuronal conduction. *Neuroscience* (Oxford, U.K.) 129, 473-479 (2004).
57. Shaqura, M. A., Zoellner, C., Mousa, S. A., Stein, C. & Schaefer, M. Characterization of µ opioid receptor binding and G protein coupling in rat hypothalamus, spinal cord, and primary afferent neurons during inflammatory pain. *J. Pharmacol. Exp. Ther.* 308, 712-718 (2004).
58. Singh, M. et al. Minocycline attenuates HIV-1 infection and suppresses chronic immune activation in humanized NOD/LtsZ-scidIL-2Rγnull mice. *Immunology* 142, 562-572 (2014).
59. Szeto, G. L. et al. Minocycline attenuates HIV infection and reactivation by suppressing cellular activation in human CD4+ T cells. *J. Infect. Dis.* 201, 1132-1140 (2010).
60. Guasti, L. et al. Minocycline treatment inhibits microglial activation and alters spinal levels of endocannabinoids in a rat model of neuropathic pain. *Mol Pain* 5, 35 (2009).
61. Heinrich, P. C., Behrmann, I., Muller-Newen, G., Schaper, F. & Graeve, L. Interleukin-6-type cytokine signaling through the gp 130/Jak/STAT pathway. *Biochem. J.* 334, 297-314 (1998).
62. Imamura, S. et al. Discovery of a Piperidine-4-carboxamide CCR5 Antagonist (TAK-220) with Highly Potent Anti-HIV-1 Activity. *J. Med. Chem.* 49, 2784-2793 (2006).
63. Akgun, E. et al. Induction of heterodimerization of mu opioid peptide (MOP) and type-2 cholecystokinin (CCK2) receptor by novel bivalent ligands. *Drugs Fut.* 2008, 33(*Suppl. A*): XXth Int Symp Med Chem (August 31-September 4, Vienna). (2008).
64. D'AMOUR, F. E. & SMITH, D. L. A METHOD FOR DETERMINING LOSS OF PAIN SENSATION. *J. Pharmacol. Exp. Ther.* 72, 74-79 (1941).
65. Dewey, W. L., Harris, L. S., Howes, J. F. & Nuite, J. A. Effect of various neurohumoral modulators on the activity of morphine and the narcotic antagonists in the tail-flick and phenylquinone tests. *J. Pharmacol. Exp. Ther.* 175, 435-442 (1970).
66. Harris, L. S. & Pierson, A. K. Narcotic antagonists in the benzomorphan series. *J. Pharmacol. Exp. Ther.* 143, 141-148 (1964).
67. Hylden, J. L. & Wilcox, G. L. Intrathecal morphine in mice: a new technique. *Eur. J Pharmacol.* 67, 313-316 (1980).
68. Schrodinger Modeling Suite Package: Maestro, Biolumintate, Glide, Prime, Macromodel, Liaison, Strike, Jaguar (2013).
69. Wilson, D. J. et al. A continuous fluorescence displacement assay for BioA: An enzyme involved in biotin biosynthesis. *Anal. Biochem.* 416, 27-38 (2011).
70. Zhang, Y., Sham, Y. Y., Rajamani, R., Gao, J. & Portoghese, P. S. Homology modeling and molecular dynamics simulations of the mu opioid receptor in a membrane-aqueous system. *ChemBioChem* 6, 853-859 (2005).
71. Jorgensen, W. L., Maxwell, D. S. & Tirado-Rives, J. Development and Testing of the OPLS All-Atom Force Field on Conformational Energetics and Properties of Organic Liquids. *J Am. Chem. Soc.* 118, 11225-11236 (1996).
72. Still, W. C., Tempczyk, A., Hawley, R. C. & Hendrickson, T. Semianalytical treatment of solvation for molecular mechanics and dynamics *J. Am. Chem. Soc.* 112, 6127-6129 (1990).
73. Jorgensen, W. L., Chandrasekhar, J., Madura, J. D., Impey, R. W. & Klein, M. L. Comparison of simple potential functions for simulating liquid water. *J. Chem. Phys.* 79, 926-935 (1983).
74. Desmond Molecular Dynamics System v3.0 (2011).

Example 2

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I or a salt thereof:

A-L-B     I wherein:

A is a residue of A1 or a stereoisomer thereof or A2:

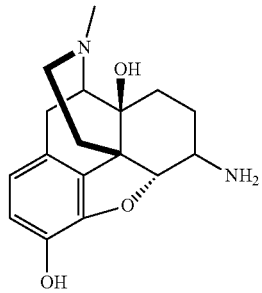

A1

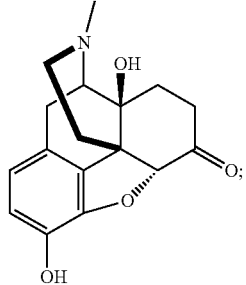

A2

B is a residue of B1:

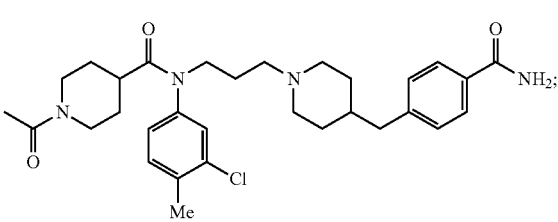

B1 and

L is a linker;

wherein the residue of A1 or A2 is derivable by the removal of a hydrogen from a heteroatom of A1 or A2 and wherein the residue of B1 is derivable by the removal of a hydrogen from a heteroatom or an alkyl group of B1.

2. The compound of claim 1, wherein A is a residue of A1.

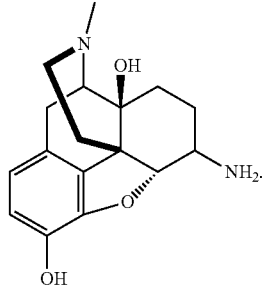

A1

3. The compound of claim 1, wherein A is a residue of A1a:

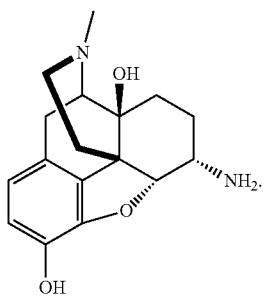

Ala

4. The compound of claim 1, wherein the residue of A1 is derivable by the removal of a hydrogen from the —NH₂ group of A1.

5. The compound of claim 1, wherein the residue of B1 is derivable by the removal of a hydrogen from the —C(=O)CH₃ group of B1.

6. The compound of claim 1 which is a compound of formula Ia:

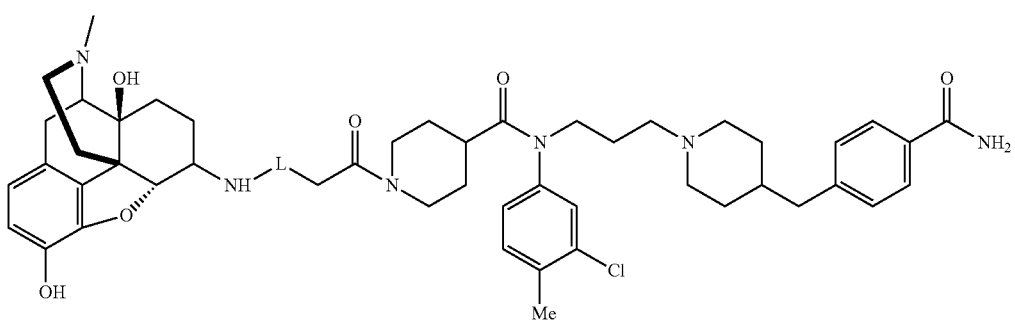

Ia or a salt thereof.

7. The compound of claim 1 which is a compound of formula Ib:

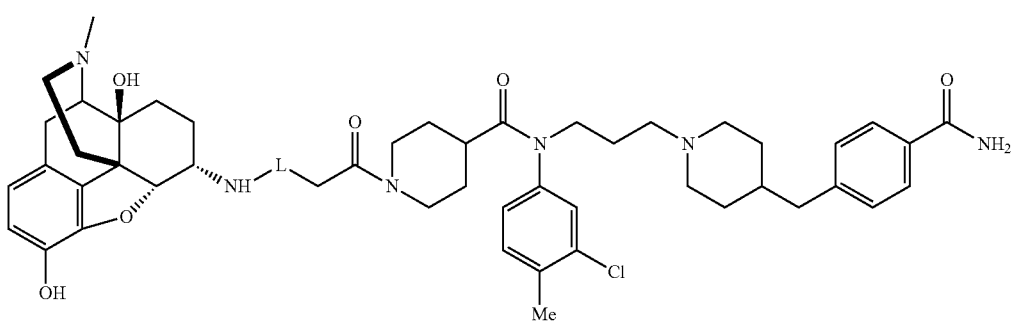

Ib or a salt thereof.

8. The compound of claim 1, wherein the linker comprises about 15 to about 300 atoms.

9. The compound of claim 1, wherein the linker comprises atoms selected from H, halo, C, O, N and S.

10. The compound of claim 1, wherein the linker is a $(C_6\text{-}C_{50})$ saturated or unsaturated hydrocarbon chain which chain is branched or unbranched, wherein one or more of the carbon atoms of the chain is replaced by a carbonyl, thiocarbonyl, O, N or S.

11. The compound of claim 1, wherein the linker is represented by formula II:

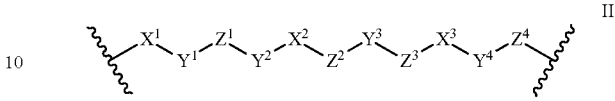

II wherein:

$X^1$ is

or absent;

$Y^1$ is $(C_1\text{-}C_6)$alkyl;
$Z^1$ is O, $NR^a$ or absent;
$Y^2$ is $(C_1\text{-}C_6)$alkyl;

$X^2$ is

or absent;
$Z^2$ is O, $NR^a$ or absent;

$Y^3$ is $(C_1-C_{20})$alkyl;
$Z^3$ is O, $NR^a$ or absent;
$X^3$ is
or absent;
$Y^4$ is $(C_1-C_6)$alkyl;
$Z^4$ is O, $NR^a$ or absent; and
each $R^a$ is independently H or $(C_1-C_6)$alkyl.
12. The compound of claim 1, wherein the linker is:
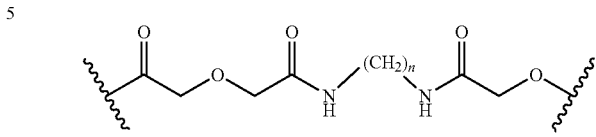
wherein n is 2, 5, 7, 9 or 10.
13. The compound of claim 1 which is:
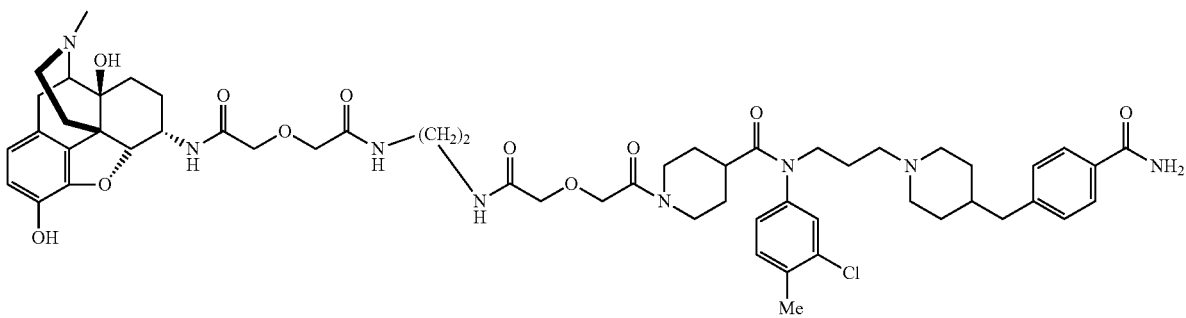
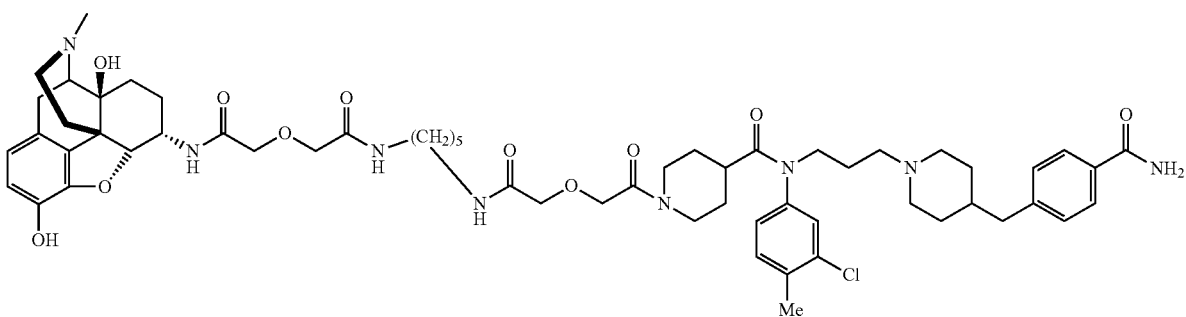
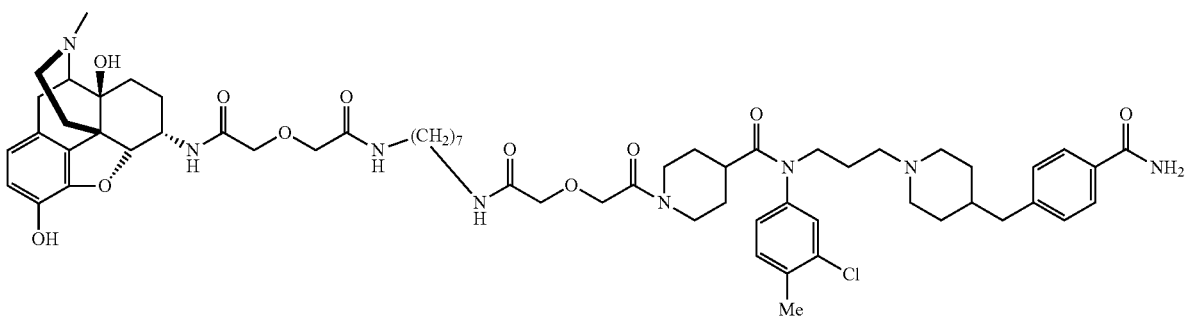
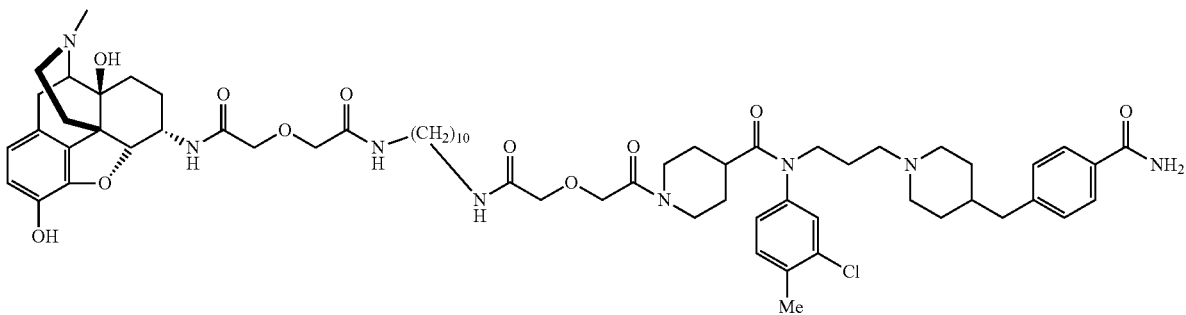

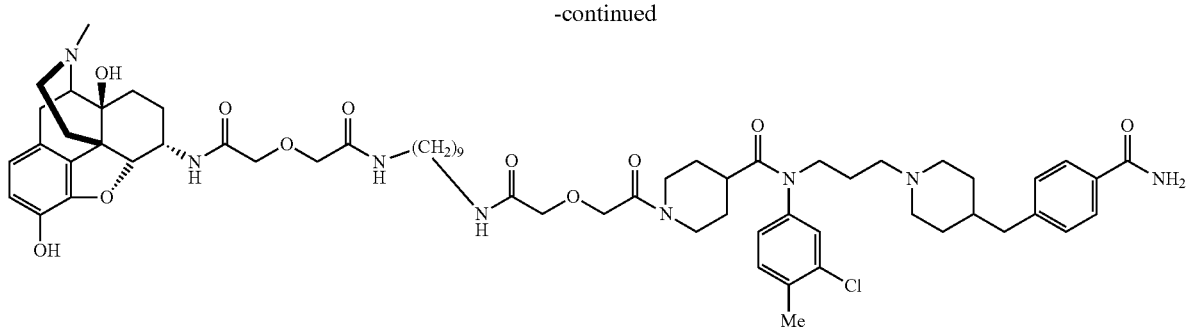

or a salt thereof.

14. A pharmaceutical composition comprising a compound of formula I as described in claim 1, or a pharmaceutically acceptable salt thereof and a pharmaceutically acceptable carrier.

15. A method of treating pain in an animal comprising administering to the animal in need thereof a compound of formula I or a pharmaceutically acceptable salt thereof as described in claim 1.

16. The method of claim 15, wherein the pain is inflammatory pain or neuropathic pain.

17. The method of claim 16, wherein the neuropathic pain is associated or induced by disease, trauma or drug use in the animal.

18. The method of claim 16, wherein the neuropathic pain is associated or induced by sickle cell anemia, diabetes, HIV, cancer, neurodegenerative disease drug use.

* * * * *